(12) United States Patent
Gokarn et al.

(10) Patent No.: US 6,455,284 B1
(45) Date of Patent: Sep. 24, 2002

(54) **METABOLICALLY ENGINEERED *E. COLI* FOR ENHANCED PRODUCTION OF OXALOACETATE-DERIVED BIOCHEMICALS**

(75) Inventors: Ravi R. Gokarn, Plymouth, MN (US); Mark A. Eiteman; Elliot Altman, both of Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/417,557

(22) Filed: Oct. 13, 1999

Related U.S. Application Data

(63) Continuation-in-part of application No. PCT/US99/08014, filed on Apr. 13, 1999.
(60) Provisional application No. 60/081,598, filed on Apr. 13, 1998, and provisional application No. 60/082,850, filed on Apr. 23, 1998.

(51) Int. Cl.$^7$ .............................. C12P 21/04; C12P 1/00; C12P 7/46
(52) U.S. Cl. .......................... 435/71.2; 435/41; 435/45; 435/71.1
(58) Field of Search ...................... 435/41, 145, 320.1, 435/135, 136, 108, 109, 113, 114, 115, 116, 71.1, 71.2, 252.32, 252.33

(56) References Cited

U.S. PATENT DOCUMENTS

| | | | |
|---|---|---|---|
| 3,580,810 A | 5/1971 | Shiio et al. | 435/115 |
| 4,601,829 A | 7/1986 | Kaneko et al. | 210/638 |
| 4,874,700 A | 10/1989 | Seipenbusch | 204/542 |
| 5,143,833 A | 9/1992 | Datta | 435/145 |
| 5,143,834 A | 9/1992 | Glassner et al. | 435/145 |
| 5,876,983 A | 3/1999 | Sugimoto et al. | 435/106 |

FOREIGN PATENT DOCUMENTS

| | | |
|---|---|---|
| DE | 197 43 894.6 | 10/1997 |
| DE | 198 31 609 | 4/1999 |
| DE | 199 04 794 | 8/2000 |
| EP | 0 405 707 | 1/1991 |
| EP | 0 723 011 | 7/1996 |
| WO | WO 99/18228 | 4/1999 |
| WO | WO 99/53035 | 10/1999 |
| WO | WO 00/39305 | 7/2000 |
| WO | WO 00/46378 | 8/2000 |

OTHER PUBLICATIONS

Chang et al., "Construction and Characterization of Amplifiable Multicopy DNA Cloning Vehicles Derived from the P15A Cryptic Miniplasmid," *J. Bacteriol.*, 134(3):1141–1156 (1978).

Horn et al., "High volumetric yields of functional dimeric miniantibodies in *Escherichia coli*, using an optimized expression vector and high–cell–density fermentation under non–limited growth conditions," *Appl. Microbiol. Biotechnol.*, 46(5–6):524–532 (1996).

Irani et al., "Improvement of the Primary Metabolism of Cell Cultures by Introducing a Pyruvate Carboxylase Reaction Way," 216$^{th}$ National Meeting, American Chemical Society, Boston, MA, *Abstracts of Papers*, Part 1, Abstract 071, vol. 216, pp. Biot71–72 (Aug. 23–27, 1998).

Irani et al., "Improvement of the Primary Metabolism of Cell Cultures by Introducing a New Cytoplasmic Pyruvate Carboxylase Reaction," *Biotechnol. Bioeng.*, 66(4):238–246 (Dec. 20, 1999).

Jensen et al., "Production of Recombinant Human Growth Hormone in *Escherichia coli*: Expression of Different Precursors and Physiological Effects of Glucose, Acetate, and Salts," *Biotechnol. Bioeng.*, 36:1–11 (1990).

Kitamoto et al., "Construction of Uracil and Tryptophan Auxotropic Mutants from Sake Yeasts by Disruption of URA3 and TRP1 Genes," *Agric. Biolog. Chem.*, 54(11):2979–2987 (1990).

McKnight et al., "Selection of functional cDNAs by complementation in yeast," *Proc. Natl. Acad. Sci. USA*, 80(14):4412–4416 (1983).

Nagashima et al., "A Novel Culture Method for High Level Production of Heterologous Protein in *Saccharomyces cerevisiae*," *Biosci. Biotechnol. Biochem.*, 58(7):1292–1296 (1994).

National Center for Biotechnology Information, National Library of Medicine, National Institutes of Health, GenBank Locus SCPYC2G, Accession No. X59890, "*S. cerivisiae* PYC2 gene for pyruvate caraboxylase," [online]. Bethesda, MD [retrieved on Feb. 2, 2001]. Retrieved from the Internet:<URL:http://www.ncbi.nlm.nih.gov/query-.fcgi?cmd=Retrieve&db=Nucleotide&list_uids=4254&dopt=GenBank>, 4 pages.

National Center for Biotechnology Information, National Library of Medicine, National Institutes of Health, GenBank Locus YSCPCB, Accession No. J03889, M16595, "Yeast (*S. cerevisiae*) pyruvate carboxylase subunit 4 (pyv) gene, complete cds.," [online]. Bethesda, MD [retrieved on Feb. 2, 2001]. Retrieved from the Internet:<URL:http://www.ncbi.nlm.nih.gov/query.fcgi?cmd=Retrieve&db=Nucleotide&list_uids=172101&dopt=GenBank>, 3 pages.

National Center for Biotechnology Information, National Library of Medicine, National Institutes of Health, GenBank Locus HUMPCB, Accession No. K02282, "Human pyruvate carboxylase gene (pcb), 3' end," [online]. Bethesda, MD [retrieved on Feb. 2, 2001]. Retrieved from the Internet:<URL:http://www.ncbi.nlm.nih.gov/query-.fcgi?cmd=Retrieve&db=Nucleotide&list_uids=189655&dopt=GenBank>, 2 pages.

(List continued on next page.)

*Primary Examiner*—Deborah Crouch
*Assistant Examiner*—Joseph Woitach
(74) *Attorney, Agent, or Firm*—Mueting, Raasch & Gebhardt, P.A.

(57) ABSTRACT

Metabolic engineering is used to increase the carbon flow toward oxaloacetate to enhance production of bulk biochemicals, such as lysine and succinate, in bacterial fermentations. Carbon flow is redirected by genetically engineering the cells to overexpress the enzyme pyruvate carboxylase.

10 Claims, 13 Drawing Sheets

OTHER PUBLICATIONS

National Center for Biotechnology Information, National Library of Medicine, National Institutes of Health, GenBank Locus REU51439, Accession No. U51439, "*Rhizobium etli* pyruvate carboxylase (PYC) gene, complete cds.," [online]. Bethesda, MD [retrieved on Feb. 2, 2001]. Retrieved from the Internet:<URL:http://www.ncbi.nlm.nih.gov/query-.fcgi?cmd=Retrieve&db=Nucleotide&list_uids=1256797&dopt=GenBank>, 3 pages.

National Center for Biotechnology Information, National Library of Medicine, National Institutes of Health, GenBank Locus RNU81515, Accession No. U81515, "*Rattus norvegicus* pyruvate carboxylate gene, promoter region," [online]. Bethesda, MD [retrieved on Feb. 2, 2001]. Retrieved from the Internet:<URL:http://www.ncbi.nlm.nih.gov/query-.fcgi?cmd=Retrieve&db=Nucleotide&list_uids=2326186&dopt=GenBank>, 2 pages.

National Center for Biotechnology Information, National Library of Medicine, National Institutes of Health, GenBank Locus D83706, Accession No. D83706, "*Bacillus stearothermophilus* DNA for pyruvate carboxylase, complete cds.," [online]. Bethesda, MD [retrieved on Feb. 2, 2001]. Retrieved from the Internet:<URL:http://www.ncbi.nlm.nih.gov/query.fcgi?cmd=Retrieve&db=Nucleotide&list_uids=1695685&dopt=GenBank>, 3 pages.

National Center for Biotechnology Information, National Library of Medicine, National Institutes of Health, GenBank Locus CGPYC, Accession No. Y09548, "*Corynebacterium glutamicum* pyc gene," [online]. Bethesda, MD [retrieved on Feb. 2, 2001]. Retrieved from the Internet:<URL:http://www.ncbi.nlm.nih.gov/query.fcgi?cmd=Retrieve&db=Nucleotide&list_uids=2879822&dopt=GenBank>, 3 pages.

National Center for Biotechnology Information, National Library of Medicine, National Institutes of Health, GenBank Locus D78170, Accession No. D78170, "Yeast DNA for pyruvate carboxylase, complete cds.," [online]. Bethesda, MD [retrieved on Feb. 2, 2001]. Retrieved from the Internet:<URL:http://www.ncbi.nlm.nih.gov/query.fcgi?cmd=Retrieve&db=Nucleotide&list_uids=1695642&dopt=GenBank>, 3 pages.

Pardee et al., "The Genetic Control and Cytoplasmic Expression of "Inducibility" in the Synthesis of β–galactosidase by *E. Coli*," *J. Mol. Biol.*, 1:165–178 (1959).

Park et al., "Elucidation of anaplerotic pathways in *Corynebacterium glutamicum* via $^{13}$C–NMR spectroscopy and GC–MS," *Appl. Microbiol. Biotechnol.*, 47: (1997).

Rodriguez et al., *Recombinant DNA Techniques: An Introduction*, Addison–Wesley Publishing, Reading, MA, Title page, publication page, and table of contents only, 7 pages (1983).

Sala–Trepat et al., "The meta Cleavage of Catechol by Azotobacter Species 4–Oxalocrotonate Pathway," *Eur. J. Biochem.*, 20(3):400–413 (1971).

Schena et al., "Vectors for Constitutive and Inducible Gene Expression in Yeast," *Meth. Enzymol.*, 194:389–398 (1991).

Shiio et al., "Glutamic Acid Formation From Glucose by Bacteria. III. On the Pathway of Pyruvate Formation in *Brevibacterium Flavum* No. 2247," *J. Biochem.*, 47(4):414–421 (1960).

Zukowski et al., "Chromogenic identification of genetic regulatory signals in *Bacillus subtilis* based on expression of a cloned Pseudomonas gene," *Proc. Natl. Acad. Sci. USA*, 80(4):1101–1105 (1983).

Eikmanns et al., "A family of *Corynebacterium glutamicum*/ *Escherichia coli* shuttle vectors for cloning, controlled gene expression, and promoter probing," *Gene*, 1991, 102:94–98.

International Search Report, International Application No. PCT/US00/28578 (Oct. 13, 2000).

National Center for Biotechnology Information, National Library of Medicine, National Institutes of Health, Bethesda, MD. GenBank Locus ECPPCG, Accession No. x05903, *E. coli* ppc gene forphosphoenolpyruvate carboxylase (EC 4.1.1.31) 1993:<URL:http://www.ncbi.nlm.nih-.gov/entrez/query.fcgi?cmd=Retrieve&db=Nucleotide&list_uids=48665&dopt=GenBank>, 2 pg.

Al–ssum et al., "Activities of Anaplerotic Enzymes and Acetyl Coenzyme A Carboxylase in Biotin–deficient *Bacillus megaterium*," *J. Gen. Microbiol.*, 100:203–206 (1977).

Altman et al., "S Gene Product: Identification and Membrane Localization of a Lysis Control Protein," *J. Bacteriol.*, 155(3):1130–1137 (1983).

Amann et al., "Tightly regulated tac promoter vectors useful for the expression of unfused and fused proteins in *Escherichia coli*," *Gene*, 69:301–315 (1988).

Attwood, "The Structure and the Mechanism of Action of Pyruvate Carboxylase," *Int. J. Biochem. Cell Biol.*, 27(3):231–249 (1995).

Barker et al., "Genetic and Biochemical Characterization of the birA Gene and Its Product: Evidence for a Direct Role of Biotin Holoenzyme Synthetase in Repression of the Biotin Operon in *Escherichia coli*," *J. Mol. Biol.*, 146:469–492 (1981).

Brosius et al., "Gene Organization and Primary Structure of a Ribosomal RNA Operon from *Escherichia coli*," *J. Mol. Biol.*, 148:107–127 (1981).

Bunch et al., "The ldhA gene encoding the fermentative lactate dehydrogenase of *Escherichia Coli*," *Microbiol.*, 143:187–195 (1997).

Cao et al., "Production of Fumaric Acid by Immobilized Rhizopus Using Rotary Biofilm Contactor," *Appl. Biochem. Biotechnol.*, 63–65:387–394 (1997).

Carroll et al., "Membrane Protein Variations Associated with In Vitro Passage of *Borrelia burgdorferi*," *Infect. Immun.*, 64(2):392–398 (1996).

Casadaban et al., "Analysis of Gene Control Signals by DNA Fusion and Cloning in *Escherichia coli*," *J. Mol. Biol.*, 138:179–207 (1980).

Cazzulo et al., "Effects of Adenosine Phosphates and Nicotinamide Nucleotides on Pyruvate Carboxylase from Baker's Yeast," *Biochem. J.*, 112:755–762 (1969).

Chao et al., "Alteration of Growth Yield by Overexpression of Phosphoenolpyruvate Carboxylase and Phosphoenolpyruvate Carboxykinase in *Escherichia coli*," *Appl. Env. Microbiol.*, 59(12):4261–4265 (1993).

Chin et al., "Altered Transcriptional Patterns Affecting Several Metabolic Pathways in Strains of *Salmonella typhimurium* Which Overexpress the Fructose Regulon," *J. Bacteriol.*, 171(5):2424–2434 (1989).

Clark, "The fermentation pathways of *Escherichia coli*," *FEMS Microbiol. Rev.*, 63:223–234 (1989).

Cremer et al., "Control of the Lysine Biosynthesis Sequence in *Corynebacterium glutamicum* as Analyzed by Overexpression of the Individual Corresponding Genes," *Appl. Env. Microbiol.*, 57(6):1746–1752 (1991).

Cronan Jr., "Expression of the Biotin Biosynthetic Operon of *Escherichia coli* Is Regulated by the Rate of Protein Biotination," *J. Biol. Chem.*, 263(21):10332–10336 (1988).

Diaz–Ricci et al., "Effect of Alteration of the Acetic Acid Synthesis Pathway on the Fermentation Pattern of *Escherichia coli*," *Biotechnol. Bioeng.*, 38:1318–1324 (1991).

Diaz–Ricci et al., "Influence of Expression of the pet Operon on Intracellular Metabolic Fluxes of *Escherichia coli*," *Biotechnol. Bioeng.*, 39:59–65 (1992).

Diesterhaft et al., "Role of Pyruvate Carboxylase, Phosphoenolpyruvate Carboxykinase, and Malic Enzyme during Growth and Sporulation of *Bacillus subtilis*," *J. Biol. Chem.*, 248(17):6062–6070 (1973).

Du et al., "Fumaric Acid Production in Airlift Loop Reactor with Porous Sparger," *Appl. Biochem. Biotech.*, 63–65:541–556 (1997).

Dunn et al., "Pyruvate Carboxylase from *Rhizobium etli*: Mutant Characterization, Nucleotide Sequence, and Physiological Role," *J. Bacteriol.*, 178(20):5960–5970 (1996).

Eikmanns et al., "A family of *Corynebacterium glutamicum/Escherichia coli* shuttle vectors for cloning, controlled gene expression, and promoter probing," *Gene*, 102:93–98 (1991).

Eiteman et al., "Optimization of the ion–exchange analysis of organic acids from fermentation," *Anal. Chim. Acta.*, 338:69–75 (1997).

Eiteman et al., "Metabolic Engineering of *E. coli* to Alter Distribution of Fermentation Products," *Proceedings of the Institute of Biological Engineering*, 1:B96–B101 (Jul., 1998).

Eiteman et al., "Overexpression of Pyruvate Carboxylase to Divert Carbon Flow Toward Oxaloacetate," $217^{th}$ Meeting of the Am. Chem. Soc., Mar. 21–25, 1999, *Abstracts of Papers Am. Chem. Soc.*, 217(1–2): Abstract 031 (1999).

Encarnación et al., "Fermentative and Aerobic Metabolism in *Rhizobium etli*," *J. Bacteriol.*, 177(11):3058–3066 (1995).

Farmer et al., "Reduction of Aerobic Acetate Production by *Escherichia coli*," *Appl. Env. Microbiol.*, 63(8):3205–3210 (1997).

Feir et al., "Pyruvate carboxylase of *Aspergillus niger*: Kinetic study of a biotin–containing carboxylase," *Can. J. Biochem.*, 47:697–710 (1969).

Freytag et al., "Molecular Cloning of a cDNA for Human Pyruvate Carboxylase—Structural Relationship to Other Biotin–Containing Carboxylases and Regulation of mRNA Content in Differentiating Preadipocytes," *J. Biol. Chem.*, 259(20):12831–12837 (1984).

Goel et al., "Analysis of Metabolic Fluxes in Batch and Continuous Cultures of *Bacillus subtilis*," *Biotechnol. Bioeng.*, 42:686–696 (1993).

Gokarn et al., "Expression of pyruvate carboxylase enhances succinate production in *Escherichia coli* without affecting glucose uptake," *Biotechnol. Lett.*, 20(8):795–798 (Aug., 1998).

Goldie et al., "Genetic and Physiological Characterization of *Escherichia coli* Mutants Deficient in Phosphoenolpyruvate Carboxykinase Activity," *J. Bacteriol.*, 141(3):1115–1121 (1980).

Gottschalk, *Bacterial Metabolism*, second ed., Springer–Verlag, New York, Title page, publication page and table of contents only, 5 pgs. (1986).

Gubler et al., "Effects of phosphoenol pyruvate carboxylase deficiency on matabolism and lysine production in *Corynebacterium glutamicum*," *Appl. Microbiol. Biotechnol.*, 40:857–863 (1994).

Guyer et al., "Identification of a Sex–factor–affinity Site in *E. coli* as γδ," *Cold Spring Harbor Symposia on Quantitative Biology: Movable Genetic Elements*, Cold Spring Harbor Laboratory 45:135–140 (1981).

Herendeen et al., "Levels of Major Proteins of *Escherichia coli* During Growth at Different Termperatures," *J. Bacteriol.*, 139(1):185–194 (1979).

Higa et al., "$CO_2$–fixing Enzymes in *Pseudomonas fluorescens*," *J. Gen. Microbiol.*, 93:69–74 (1976).

Hill et al., "High Performance Liquid Chromatographic Determination of Amino Acids in the Picomole Range," *Anal. Chem.*, 51(8):1338–1341 (1979).

Iuchi et al., "arcA (dye), a global regulatory gene in *Escherichia coli* mediating repression of enzymes in aerobic pathways," *Proc. Natl. Acad. Sci. USA*, 85:1888–1892 (1988).

Iuchi et al., "A Second Global Regulator Gene (arcB) Mediating Repression of Enzymes in Aerobic Pathways of *Escherichia coli*," *J. Bacteriol.*, 171(2):868–873 (1989).

Jetten et al., "Metabolic Engineering of *Corynebacterium glutamicum*," *Annals NY Acad. Sci.*, 272:12–29 (1993).

Jetten et al., "Regulation of Phospho(enol)–pyruvate– and oxaloacetate–converting enzymes in *Corynebacterium glutamicum*," *Appl. Microbiol. Biotechnol.*, 41:47–52 (1994).

Jitrapakdee et al., "The Rat Pyruvate Carboxylase Gene Structure—Alternate Promoters Generate Multiple Transcripts with the 5'-End Heterogeneity," *J. Biol. Chem.*, 272(33):20522–20530 (1997).

Kiss et al., "Metabolic Characterization of a $_L$–Lysine–Producing Strain by Continuous Culture," *Biotechnol. Bioeng.*, 39(5):565–574 (1992).

Kodaki et al., "Cloning of Phosphoenolpyruvate Carboxylase Gene from a Cyanobacterium, *Anacystis nidulans*, in *Escherichia coli*," *J. Biochem.*, 97(2):533–539 (1985).

Koffas et al., "Sequence of the *Corynebacterium glutamicum* pyruvate carboxylase gene," *Appl. Microbiol. Biotechnol.*, 50:346–352 (1998).

Kondo, "Cloning and nucleotide sequence of *Bacillus stearothermophilus* pyruvate carboxylase," *Gene*, 191(1):47–50 (1997).

Kornberg, "The Role and Control of the Glyoxylate Cycle in *Escherichia coli*," *Biochem. J.*, 99:1–11 (1966).

Kroschwitz et al., eds., "Amino Acids (Survey)," *Kirk–Othmer Encyclopedia of Chemical Technology*, $4^{th}$ Ed., vol. 2, John Wiley & Sons, New York, pp. 534–570 (1992).

Libor, "Pyruvate Carboxylase from a Thermophilic Bacillus: Some Molecular Characteristics," *Biochemistry*, 18(17):3647–3653 (1979).

Lim et al., "Sequence and Domain Structure of Yeast Pyruvate Carboxylase," *J. Biol. Chem.*, 263(23):11493–11497 (1988).

Lowry et al., "Protein Measurement with the Folin Phenol Reagent," *J. Biol. Chem.*, 193:265–275 (1951).

Maloy et al., "Role of Gene fadR in *Escherichia coli* Acetate Metabolism," *J. Bacteriol.*, 148(1):83–90 (1981).

Millard et al., "Enhanced Production of Succinic Acid by Overexpression of Phosphoenolpyruvate Carboxylase in *Escherichia coli*," *Appl. Environ. Microbiol.*, 62(5):1808–1810 (1996).

Miller, *Experiments in Molecular Genetics*, Cold Spring Harbor Laboratory, New York, Title page, publication page, and table of contents only, 8 pgs. (1972).

Milrad de Forchetti et al., "Some Properties of the Pyruvate Carboxylase from *Pseudomonas Fluorescens*," *J. Gen. Microbiol.*, 93:75–81 (1976).

Modak et al., "Acetyl–CoA–dependent pyruvate carboxylase from the photosynthetic bacterium *Rhodobacter capsulatus*: rapid and efficient purification using dye–ligand affinity chromatography," *Microbiol.*, 141(10):2619–2628 (1995).

Morikawa et al., Regulation of *Escherichia coli* Phosphoenolpyruvate Carboxylase by Multiple Effectors In Vivo, *J. Biochem.*, 87(2):441–449 (1980).

Mukhopadhyay et al., "Purification, Regulation, and Molecular and Biochemical Characterization of Pyruvate Carboxylase from *Methanobacterium thermoautotrophicum* Strain ΔH," *J. Biol. Chem.*, 273(9):5155–5166 (1998).

Myers et al., "Activation of Yeast Pyruvate Carboxylase: Interactions between Acyl Coenzyme A Compounds, Aspartate and Substrates of the Reaction," *Biochemistry*, 22(22):5090–5096 (1983).

Norrander et al., "Construction of improved M13 vectors using oligonucleotide–directed mutagenesis," *Gene*, 26:101–106 (1983).

O'Brien et al., "Novel Enzymatic Machinery for the Metabolism of Oxaloacetate, Phosphoenolpyruvate, and Pyruvate in *Pseudomonas citronellolis*," *J. Biol. Chem.*, 252(4):1257–1263 (1977).

Papoutsakis et al., "Equations and Calculations of Product Yields and Preferred Pathways for Butanediol and Mixed–Acid Fermentations," *Biotechnol. Bioeng.*, 27:50–66 (1985).

Park et al., "Metabolic and Physiological Studies of *Corynebacterium glutamicum* Mutants," *Biotechnol. Bioeng.*, 55(6):864–879 (1997).

Payne et al., "Pyruvate Carboxylase in *Rhodopseudomonas spheroides*," *J. Gen. Microbiol.*, 59:97–101 (1969).

Peters–Wendisch, "Anaplerotische Reaktionen in *Corynebacterium glutamicum:* Unterschungen zur Bedeutung der PEP–Carboxylase und der Pyruvat–Carboxylase im Zentralstoffwechsel und bei der Aminosäure–Produktion," Institut für Biotechnologie, D61 Diss. Universität Düsseldorf, Bundesrepublik Deutschland, Aug., 1996 and English language Abstract, "Anaplerotic reactions in *Corynebacterium glutamicum*. Studies of the significance of phosphoenolpyruvate (PEP)–carboxylase and pyruvate carboxylase in the central metabolism and in amino acid production," *Chemical Abstracts*, 26(12) Abstract No. 154946 (1997).

Peters–Wendisch et al., "Pyruvate carboxylase as an anaplerotic enzyme in *Corynebacterium glutamicum*," *Microbiology*, 143:1095–1103 (1997).

Peters–Wendisch et al., "Pyruvate carboxylase from *Corynebacterium glutamicum:* characterization, expression and inactivation of the pyc gene," *Microbiology*, 144:915–927 (Apr. 6, 1998).

Pines et al., "Overexpression of cytosolic malate dehydrogenase (MDH2) causes overproduction of specific organic acids in *Saccharomyces cerevisiae*," *Appl. Microbiol. Biotechnol.*, 48: 248–255 (1997).

Reardon et al., "Metabolic Pathway Rates and Culture Fluorescence in Batch Fermentations of *Clostridium Acetobutylicum*," *Biotechnol. Prog.*, 3(3):153–167 (1987).

Sawers et al., "Anaerobic Regulation of Pyruvate Formate–Lyase from *Escherichia coli* K–12," *J. Bacteriol.*, 170(11):5330–5336 (1988).

Schilling, "Chemicals from alternative feedstocks in the United States," *FEMS Microbiol. Rev.*, 16:101–110 (1995).

Scrutton et al., "Isolation and Characterization of Pyruvate Carboxylase from *Azotobacter vinelandii* OP," *Arch. Biochem. Biophys.*, 164:641–654 (1974).

Shiio et al., "Glutamic Acid Formation From Glucose by Bacteria. IV. Carbon Dioxide Fixation and Glutamate Formation in *Brevibacterium Flavum* No. 2247," *J. Biochem.*, 48(1):110–120 (1960).

Shiio et al., "Microbial Production of L–Threonine. Part I. Production by *Escherichia coli* Mutant Resistant to α–Amino–β–hydroxyvaleric Acid," *Agr. Biol. Chem.*, 33(8):1152–1160 (1969).

Stephanopoulos et al., "Network Rigidity and Metabolic Engineering in Metabolite Overproduction," *Science*, 252:1675–1681 (1991).

Stols et al., "Expression of *Ascaris suum* Malic Enzyme in a Mutant *Escherichia coli* Allows Production of Succinic Acid from Glucose," *Appl. Biochem. Biotechnol.*, 63–65:153–158 (1997).

Stols et al., "Production of Succinic Acid through Overexpression of $NAD^+$–Dependent Malic Enzyme in an *Escherichia coli* Mutant," *Appl. Environ Microbiol.*, 63(7):2695–2701 (1997).

Stucka et al., "DNA sequences in chromosomes II and VII code for pyruvate carboxylase isoenzymes in *Saccharomyces cerevisiae:* analysis of pyruvate carboxylase–deficient strains," *Mol. Gen. Genet.*, 229(2):307–315 (1991).

Sunnarborg et al., "Regulation of the Glyoxylate Bypass Operon: Cloning and Characterization of iclR," *J. Bacteriol.*, 172(5):2642–2649 (1990).

Švedas et al., "The Interaction of Amino Acids with o–Phthaldialdehyde: A Kinetic Study and Spectrophotometric Assay of the Reaction Product," *Anal. Biochem.*, 101:188–195 (1980).

Terada et al., "Site–Directed Mutagenesis of Phosphoenolpyruvate Carboxylase from *E. coli:* The Role of $His^{579}$ in the Catalytic and Regulatory Functions," *J. Biochem.*, 109(1):49–54 (1991).

Utter et al., "Chapter 4. Formation of Oxalacetate by $CO_2$ Fixation on Phosphoenolpyruvate," *The Enzymes*, Third ed., Boyer, ed., Academic Press, New York, 6:117–135 (1972).

Vallino et al., "Ch. 18: Flux Determination in Cellular Bioreaction Networks: Applications to Lysine Fermentations," *Frontiers in Bioprocessing*, Sikdar et al., eds., CRC Press, Inc., Boca Raton, pp. 205–219 (1990).

Vallino et al., "Metabolic Flux Distributions in *Corynebacterium glutamicum* During Growth and Lysine Overproduction," *Biotechnol. Bioeng.*, 41(6):633–646 (1993).

Varma et al., "Metabolic Capabilities of *Escherichia coli:* I. Synthesis of Biosynthetic Precursors and Cofactors," *J. Theor. Biol.*, 165:477–502 (1993).

Wallace et al., "Molecules in Focus—Pyruvate Carboxylase," *Int. J. Biochem. Cell Biol.*, 30:1–5 (1998).

Willison, "Pyruvate and Acetate Metabolism in the Photosynthetic Bacterium *Rhodobacter capsulatus*," *J. Gen. Microbiol.*, 134:2429–2439 (1988).

METABOLICALLY ENGINEERED *E. COLI* FOR ENHANCED PRODUCTION OF OXALOACETATE-DERIVED BIOCHEMICALS

This application is a continuation-in-part application of International Application PCT/US99/08014, with an international filing date of Apr. 13, 1999, which in turn claims the benefit of U.S. Provisional Application No. 60/081,598, filed Apr. 13, 1998, and U.S. Provisional Application No. 60/082,850, filed Apr. 23, 1998.

BACKGROUND OF THE INVENTION

Tremendous commercial potential exists for producing oxaloacetate-derived biochemicals via aerobic or anaerobic bacterial fermentation processes. Aerobic fermentation processes can be used to produce oxaloacetate-derived amino acids such as asparagine, aspartate, methionine, threonine, isoleucine, and lysine. Lysine, in particular, is of great commercial interest in the world market. Raw materials comprise a significant portion of lysine production cost, and hence process yield (product generated per substrate consumed) is an important measure of performance and economic viability. The stringent metabolic regulation of carbon flow (described below) can limit process yields. Carbon flux towards oxaloacetate (OAA) remains constant regardless of system perturbations (J. Vallino et al., *Biotechnol. Bioeng.*, 41, 633–646 (1993)). In one reported fermentation, to maintain this rigid regulation of carbon flow at the low growth rates desirable for lysine production, the cells converted less carbon to oxaloacetate, thereby limiting the lysine yield (R. Kiss et al., *Biotechnol. Bioeng.*, 39, 565–574 (1992)). Hence, a tremendous opportunity exists to improve the process by overcoming the metabolic regulation of carbon flow.

Anaerobic fermentation processes can be used to produce oxaloacetate-derived organic acids such as malate, fumarate, and succinate. Chemical processes using petroleum feedstock can also be used, and have historically been more efficient for production of these organic acids than bacterial fermentations. Succinic acid in particular, and its derivatives, have great potential for use as specialty chemicals. They can be advantageously employed in diverse applications in the food, pharmaceutical, and cosmetics industries, and can also serve as starting materials in the production of commodity chemicals such as 1,4-butanediol and tetrahydrofuran (L. Schilling, *FEMS Microbiol. Rev.*, 16, 101–110 (1995)). Anaerobic rumen bacteria have been considered for use in producing succinic acid via bacterial fermentation processes, but these bacteria tend to lyse during the fermentation. More recently, the strict anaerobe *Anaerobiospirillum succiniciproducens* has been used, which is more robust and produces higher levels of succinate (R. Datta, U.S. Pat. No. 5,143,833 (1992); R. Datta et al., Eur. Pat. Appl. *405707* (1991)).

Commercial fermentation processes use crop-derived carbohydrates to produce bulk biochemicals. Glucose, one common carbohydrate substrate, is usually metabolized via the Embden-Meyerhof-Parnas (EMP) pathway, also known as the glycolytic pathway, to phosphoenolpyruvate (PEP) and then pyruvate. All organisms derive some energy from the glycolytic breakdown of glucose, regardless of whether they are grown aerobically or anaerobically. However, beyond these two intermediates, the pathways for carbon metabolism are different depending on whether the organism grows aerobically or anaerobically, and the fates of PEP and pyruvate depend on the particular organism involved as well as the conditions under which metabolism is taking place.

In aerobic metabolism, the carbon atoms of glucose are oxidized fully to carbon dioxide in a cyclic process known as the tricarboxylic acid (TCA) cycle or, sometimes, the citric acid cycle, or Krebs cycle. The TCA cycle begins when oxaloacetate combines with acetyl-CoA to form citrate. Complete oxidation of glucose during the TCA cycle ultimately liberates significantly more energy from a single molecule of glucose than is extracted during glycolysis alone. In addition to fueling the TCA cycle in aerobic fermentations, oxaloacetate also serves as an important precursor for the synthesis of the amino acids asparagine, aspartate, methionine, threonine, isoleucine and lysine. This aerobic pathway is shown in FIG. 1 for *Escherichia coli*, the most commonly studied microorganism. Anaerobic organisms, on the other hand, do not fully oxidize glucose. Instead, pyruvate and oxaloacetate are used as acceptor molecules in the reoxidation of reduced cofactors (NADH) generated in the EMP pathway. This leads to the generation and accumulation of reduced biochemicals such as acetate, lactate, ethanol, formate and succinate. This anaerobic pathway for *E. coli* is shown in FIG. 2.

Intermediates of the TCA cycle are also used in the biosynthesis of many important cellular compounds. For example, α-ketoglutarate is used to biosynthesize the amino acids glutamate, glutamine, arginine, and proline, and succinyl-CoA is used to biosynthesize porphyrins. Under anaerobic conditions, these important intermediates are still needed. As a result, succinyl-CoA, for example, is made under anaerobic conditions from oxaloacetate in a reverse reaction; i.e., the TCA cycle runs backwards from oxaloacetate to succinyl-CoA.

Oxaloacetate that is used for the biosynthesis of these compounds must be replenished if the TCA cycle is to continue unabated and metabolic functionality is to be maintained. Many organisms have thus developed what are known as "anaplerotic pathways" that regenerate intermediates for recruitment into the TCA cycle. Among the important reactions that accomplish this replenishing are those in which oxaloacetate is formed from either PEP or pyruvate. These pathways that resupply intermediates in the TCA cycle can be utilized during either aerobic or anaerobic metabolism.

PEP occupies a central position, or node, in carbohydrate metabolism. As the final intermediate in glycolysis, and hence the immediate precursor in the formation of pyruvate via the action of the enzyme pyruvate kinase, it can serve as a source of energy. Additionally, PEP can replenish intermediates in the TCA cycle via the anaplerotic action of the enzyme PEP carboxylase, which converts PEP directly into the TCA intermediate oxaloacetate. PEP is also often a cosubstrate for glucose uptake into the cell via the phosphotransferase system (PTS) and is used to biosynthesize aromatic amino acids. In many organisms, TCA cycle intermediates can be regenerated directly from pyruvate. For example, pyruvate carboxylase (PYC), which is found in some bacteria but not *E. coli*, mediates the formation of oxaloacetate by the carboxylation of pyruvate utilizing carboxybiotin. As might be expected, the partitioning of PEP is rigidly regulated by cellular control mechanisms, causing a metabolic "bottleneck" which limits the amount and direction of carbon flowing through this juncture. The enzyme-mediated conversions that occur between PEP, pyruvate and oxaloacetate are shown in FIG. 3.

TCA cycle intermediates can also be regenerated in some plants and microorganisms from acetyl-CoA via what is known as the "glyoxylate shunt," "glyoxylate bypass" or glyoxylate cycle (FIG. 4). This pathway enables organisms growing on 2-carbon substrates to replenish their oxaloacetate. Examples of 2-carbon substrates include acetate and other fatty acids as well as long-chain n-alkanes. These substrates do not provide a 3-carbon intermediate such as PEP which can be carboxylated to form oxaloacetate. In the glyoxylate shunt, isocitrate from the TCA cycle is cleaved into glyoxylate and succinate by the enzyme isocitrate lyase. The released glyoxylate combines with acetyl-CoA to form malate through the action of the enzyme malate synthase. Both succinate and malate generate oxaloacetate through the TCA cycle. Expression of the genes encoding the glyoxylate bypass enzymes is tightly controlled, and normally these genes are repressed when 3-carbon compounds are available. In *E. coli*, for example, the genes encoding the glyoxylate bypass enzymes are located on the aceBAK operon and are controlled by several transcriptional regulators: ic/R (A. Sunnarborg et al., *J. Bacteriol.*, 172, 2642–2649 (1990)), fad/R (S. Maloy et al., *J. Bacteriol.* 148 83–90 (1981)), fruR (A. Chia et al., *J. Bacteriol.*, 171, 2424–2434 (1989)), and arcAB (S. Iuchi et al., *J. Bacteriol.* 171 868–873 (1989); S. Iuchi et al., *Proc. Natl. Acad. Sci. USA*, 85, 1888–1892 (1988)). The glyoxylate bypass enzymes are not expressed when *E. coli* is grown on glucose, glycerol, or pyruvate as a carbon source. The glyoxylate shunt is induced by fatty acids such as acetate (Kornberg, *Biochem. J.*, 99, 1–11 (1966)).

Various metabolic engineering strategies have been pursued, with little success, in an effort to overcome the network rigidity that surrounds carbon metabolism. For example, overexpression of the native enzyme PEP carboxylase in *E. coli* was shown to increase the carbon flux towards oxaloacetate (C. Millard et al., *Appl. Environ. Microbiol.*, 62, 1808–1810 (1996); W. Farmer et al, *Appl. Env. Microbiol.*, 63, 3205–3210 (1997)); however, such genetic manipulations also cause a decrease in glucose uptake (P. Chao et al., *Appl. Env. Microbiol.*, 59, 4261–4265 (1993)), since PEP is a required cosubstrate for glucose transport via the phosphotransferase system. An attempt to improve lysine biosynthesis in *Corynebacterium glutamicum* by overexpressing PEP carboxylase was likewise not successful (J. Cremer et al., *Appl. Env. Microbiol.*, 57, 1746–1752 (1991)). In another approach to divert carbon flow toward oxaloacetate, the glyoxylate shunt in *E. coli* was derepressed by knocking out one of the transcriptional regulators, fadR. Only a slight increase in biochemicals derived from oxaloacetate was observed (W. Farmer et al., *Appl. Environ. Microbiol.*, 63, 3205–3210 (1997)). In a different approach, malic enzyme from *Ascaris suum* was overproduced in mutant *E. coli* which were deficient for the enzymes that convert pyruvate to lactate, acetyl-CoA, and formate. This caused pyruvate to be converted to malate which increased succinate production (see FIG. 2). However, this approach is problematic, since the mutant strain in question cannot grow under the strict anaerobic conditions which are required for the optimal fermentation of glucose to organic acids (L. Stols et al., *Appl. Biochem. Biotechnol.*, 63–65, 153–158 (1997)).

A metabolic engineering approach that successfully overcomes the network rigidity that characterizes carbon metabolism and diverts more carbon toward oxaloacetate, thereby increasing the yields of oxaloacetate-derived biochemicals per amount of added glucose, would represent a significant and long awaited advance in the field.

SUMMARY OF THE INVENTION

The present invention employs a unique metabolic engineering approach which overcomes a metabolic limitation that cells use to regulate the synthesis of the biochemical oxaloacetate. The invention utilizes metabolic engineering to divert more carbon from pyruvate to oxaloacetate by making use of the enzyme pyruvate carboxylase. This feat can be accomplished by introducing a native (i.e., endogenous) and/or foreign (i.e., heterologous) nucleic acid fragment which encodes a pyruvate carboxylase into a host cell, such that a functional pyruvate carboxylase is overproduced in the cell. Alternatively, the DNA of a cell that endogenously expresses a pyruvate carboxylase can be mutated to alter transcription of the native pyruvate carboxylase gene so as to cause overproduction of the native enzyme. For example, a mutated chromosome can be obtained by employing either chemical or transposon mutagenesis and then screening for mutants with enhanced pyruvate carboxylase activity using methods that are well-known in the art. Overexpression of pyruvate carboxylase causes the flow of carbon to be preferentially diverted toward oxaloacetate and thus increases production of biochemicals which are biosynthesized from oxaloacetate as a metabolic precursor.

Accordingly, the present invention provides a metabolically engineered cell that overexpresses pyruvate carboxylase. Overexpression of pyruvate carboxylase is preferably effected by transforming the cell with a DNA fragment encoding a pyruvate carboxylase that is derived from an organism that endogenously expresses pyruvate carboxylase, such as *Rhizobium etli, Corynebacterium glutamicum, Methanobacterium thermoautotrophicum*, or *Pseudomonas fluorescens*. Pyruvate carboxylase can be expressed within the engineered cell from an expression vector, or alternatively from a DNA fragment that has been chromosomally integrated into the cell's genome. Optionally, the metabolically engineered cell of the invention overexpresses PEP carboxylase in addition to pyruvate carboxylase. Also optionally, the metabolically engineered cell does not express a detectable level of PEP carboxykinase. In a particularly preferred embodiment of the invention, the metabolically engineered cell is a *C. glutamicum, E. coli, Brevibacterium flavum*, or *Brevibacterium lactofermentum* cell that expresses a heterologous pyruvate carboxylase.

The invention also includes a method for making a metabolically engineered cell that involves transforming a cell with a nucleic acid fragment that contains a nucleotide sequence encoding an enzyme having pyruvate carboxylase activity, to yield a metabolically engineered cell that overexpresses pyruvate carboxylase. The method optionally includes co-transforming the cell with a nucleic acid fragment that contains a nucleotide sequence encoding an enzyme having PEP carboxylase activity so that the metabolically engineered cells also overexpress PEP carboxylase.

Also included in the invention is a method for making an oxaloacetate-derived biochemical that includes providing a cell that produces the biochemical; transforming the cell with a nucleic acid fragment containing a nucleotide sequence encoding an enzyme having pyruvate carboxylase activity; expressing the enzyme in the cell to cause increased production of the biochemical; and isolating the biochemical from the cell. Preferred biochemicals having oxaloacetate as a metabolic precursor include, but are not limited to, amino acids such as lysine, asparagine, aspartate, methionine, threonine, and isoleucine; organic acids such as succinate, malate and fumarate; pyrimidine nucleotides; and porphyrins.

The invention further includes a nucleic acid fragment isolated from *P. fluorescens* which contains a nucleotide sequence encoding a pyruvate carboxylase enzyme, preferably the α4Γ4 pyruvate carboxylase enzyme produced by *P. fluorescens*.

DETAILED DESCRIPTION OF THE INVENTION

Figure 1:
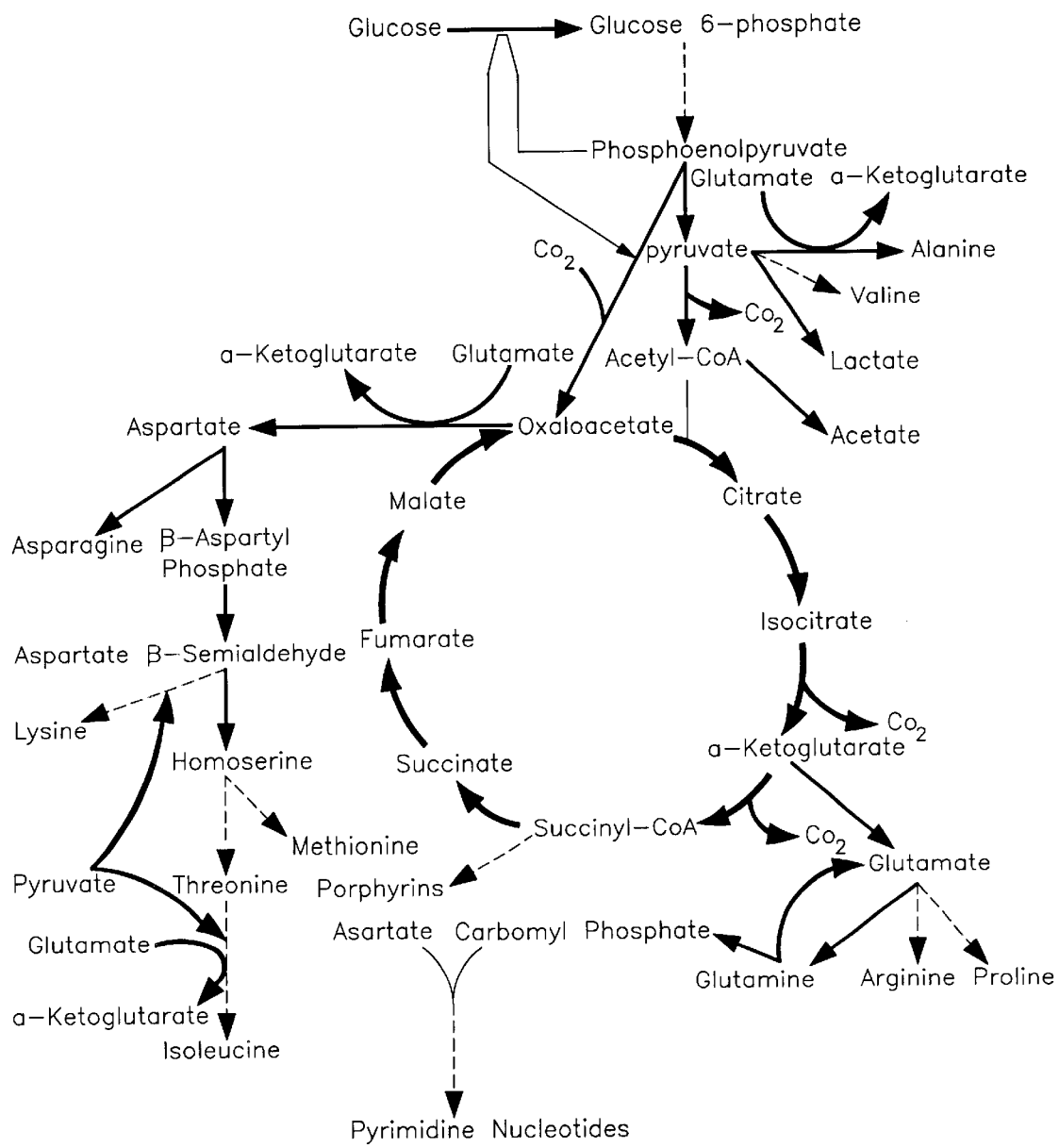
FIG. 1. Aerobic pathway in *E. coli* depicting glycolysis, the TCA cycle, and biosynthesis of oxaloacetate-derived biochemicals; dashed lines signify that multiple steps are required to biosynthesize the compound while solid lines signify a one-step conversion; the participation of PEP in glucose uptake is shown by a light line; the pathway as shown is not stoichiometric, nor does it include cofactors.

Metabolic engineering involves genetically overexpressing particular enzymes at critical points in a metabolic pathway, and/or blocking the synthesis of other enzymes, to overcome or circumvent metabolic "bottlenecks." The goal of metabolic engineering is to optimize the rate and conversion of a substrate into a desired product. The present invention employs a unique metabolic engineering approach which overcomes a metabolic limitation that cells use to regulate the synthesis of the biochemical oxaloacetate. Specifically, cells of the present invention are genetically engineered to overexpress a functional pyruvate carboxylase, resulting in increased levels of oxaloacetate.

Genetically engineered cells are referred to herein as "metabolically engineered" cells when the genetic engineering is directed to disruption or alteration of a metabolic pathway so as to cause a change in the metabolism of carbon. An enzyme is "overexpressed" in a metabolically engineered cell when the enzyme is expressed in the metabolically engineered cell at a level higher than the level at which it is expressed in a comparable wild-type cell. In cells that do not endogenously express a particular enzyme, any level of expression of that enzyme in the cell is deemed an "overexpression" of that enzyme for purposes of the present invention.

Many organisms can synthesize oxaloacetate from either PEP via the enzyme PEP carboxylase, or from pyruvate via the biotin-dependent enzyme pyruvate carboxylase. Representatives of this class of organisms include *C. glutamicum*, *R. etli*, *P. fluorescens*, *Pseudomonas citronellolis*, *Azotobacter vinelandii*, *Aspergillus nidulans*, and rat liver cells. Other organisms cannot synthesize oxaloacetate directly from pyruvate because they lack the enzyme pyruvate carboxylase. *E. coli*, *Salmonella typhimurium*, *Fibrobacter succinogenes*, and *Ruminococcus flavefaciens* are representatives of this class of organisms. In either case, the metabolic engineering approach of the present invention can be used to redirect carbon to oxaloacetate and, as a result, enhance the production of biochemicals which use oxaloacetate as a metabolic precursor.

The cell that is metabolically engineered according to the invention is not limited in any way to any particular type or class of cell. It can be a eukaryotic cell or a prokaryotic cell; it can include, but is not limited to, a cell of a human, animal, plant, insect, yeast, protozoan, bacterium, or archaebacterium. Preferably, the cell is a microbial cell, more preferably, a bacterial cell. Advantageously, the bacterial cell can be an *E. coli*, *C. glutamicum*, *B. flavum* or *B. lactofermentum* cell; these strains are currently being employed industrially to make amino acids which can be derived from oxaloacetate using bacterial fermentation processes. Mutant *E. coli* strains are currently being considered for commercial synthesis of succinate via anaerobic fermentation (L. Stols et al., *Appl. Environ. Microbiol.*, 63 2695–2701 (1997); L. Stols et al., *Appl. Biochem. Biotech.*, 63, 153–158 (1997)), although *A. succiniciproducens* has been considered in the past. Rhizopus fungi are now being considered to produce fumarate via aerobic fermentations (N. Cao, *Appl. Biochem. Biotechnol.*, 63, 387–394 (1997); J. Du et al., *Appl. Biochem. Biotech.*, 63, 541–556 (1997)). Bacteria that lack endogenous pyruvate carboxylase, such as *E. coli*, *Fibrobacter succinogenes*, and *R. flaveflaciens*, can be used in the metabolic engineering strategy described by the invention.

Optionally, the metabolically engineered cell has been engineered to disrupt, block, attenuate or inactivate one or more metabolic pathways that draw carbon away from oxaloacetate. For example, alanine and valine can typically be biosynthesized directly from pyruvate, and by inactivating the enzymes involved in the synthesis of either or both of these amino acids, oxaloacetate production can be increased. Thus, the metabolically engineered cell of the invention can be an alanine and/or a valine auxotroph, more preferably a C. glutamicum alanine and/or a valine auxotroph. Likewise, the metabolically engineered cell can be engineered to reduce or eliminate the production of PEP carboxykinase, which catalyzes the formation of PEP from oxaloacetate (the reverse of the reaction catalyzed by PEP carboxylase). Preventing or reducing the expression of a functional PEP carboxykinase will result in more carbon shunted to oxaloacetate and hence the amino acids and organic acids biosynthesized therefrom.

Another alternative involves interfering with the metabolic pathway used to produce acetate from acetyl CoA. Disrupting this pathway should result in higher levels of acetyl CoA, which may then indirectly result in increased amounts of oxaloacetate. Moreover, where the pyruvate carboxylase enzyme that is expressed in the metabolically engineered cell is one that is activated by acetyl CoA (see below), higher levels of acetyl CoA in these mutants lead to increased activity of the enzyme, causing additional carbon to flow from pyruvate to oxaloacetate. Thus, acetate-mutants. are preferred metabolically engineered cells.

The pyruvate carboxylase expressed by the metabolically engineered cell can be either endogenous or heterologous. A "heterologous" enzyme is one that is encoded by a nucleotide sequence that is not normally present in the cell. For example, a bacterial cell that has been transformed with and expresses a gene from a different species or genus that encodes a pyruvate carboxylase contains a heterologous pyruvate carboxylase. The heterologous nucleic acid fragment may or may not be integrated into the host genome. The term "pyruvate carboxylase" means a molecule that has pyruvate carboxylase activity; i.e., that is able to catalyze carboxylation of pyruvate to yield oxaloacetate. The term "pyruvate carboxylase" thus includes naturally occurring pyruvate carboxylase enzymes, along with fragments, derivatives, or other chemical, enzymatic or structural modifications thereof, including enzymes encoded by insertion, deletion or site mutants of naturally occurring pyruvate carboxylase genes, as long as pyruvate carboxylase activity is retained. Pyruvate carboxylase enzymes and, in some cases, genes that have been characterized include human pyruvate carboxylase (GenBank K02282; S. Freytag et al., *J. Biol. Chem.*, 259, 12831–12837 (1984)); pyruvate carboxylase from *Saccharomyces cerevisiae* (GenBank X59890, J03889, and M16595; R. Stucka et al., *Mol. Gen. Genet.*, 229, 307–315 (1991); F. Lim et al., *J. Biol. Chem.*, 263, 11493–11497 (1988); D. Myers et al., *Biochemistry*, 22, 5090–5096 (1983)); pyruvate carboxylase from *Schizosaccharomyces pombe* (Gen bank D78170); pyruvate carboxylase from *R. etli* (GenBank U51439; M. Dunn et al., *J. Bacteriol.*, 178, 5960–5970 (1996)); pyruvate carboxylase from *Rattus norvegicus* (GenBank U81515; S. Jitrapakdee et al., *J. Biol. Chem.*, 272, 20522–20530 (1997)); pyruvate carboxylase from *Bacillus stearothermophilus* (GenBank D83706; H. Kondo, *Gene*, 191, 47–50 (1997); S. Libor, *Biochemistry*, 18, 3647–3653 (1979)); pyruvate carboxylase from *P. fluorescens* S. Milrad de Forchetti et al., *J. Gen. Microbiol.*, 93 75–81 (1976) pyruvate carboxylase from *M thermoautotrophicum* (B. Mukhapodhyay et al., *J. Biol. Chem.*, 273, 5155–5166 (1998)); and pyruvate carboxylase from *C. glutamicum* (GenBank Y09548).

Preferably, the pyruvate carboxylase expressed by the metabolically engineered cells is derived from either *R. etli* or *P. fluorescens*. The pyruvate carboxylase in *R. etli* is encoded by the pyc gene (M. Dunn et al., *J. Bacteriol.*, 178, 5960–5970 (1996)). The *R. etli* enzyme is classified as an α4 pyruvate carboxylase, which is inhibited by aspartate and requires acetyl CoA for activation. Members of this class of pyruvate carboxylases might not seem particularly well-suited for use in the present invention, since redirecting carbon flow from pyruvate to oxaloacetate would be expected to cause reduced production of acetyl CoA, and increased production of aspartate, both of which will decrease pyruvate carboxylase activity. However, expression of *R. etli* pyruvate carboxylase in a bacterial host is shown herein to be effective to increase production of oxaloacetate and its downstream metabolites (see Examples I and II). Moreover, this can be accomplished without adversely affecting glucose uptake by the host (see Example III) which has been the stumbling block in previous efforts to divert carbon to oxaloacetate by overexpressing PEP carboxylase (P. Chao et al., *Appl. Env. Microbiol.*, 59 4261–4265 (1993)).

In a particularly preferred embodiment, the metabolically engineered cell expresses an α4β4 pyruvate carboxylase. Members of this class of pyruvate carboxylases do not require acetyl CoA for activation, nor are they inhibited by aspartate, rendering them particularly well-suited for use in the present invention. *P. fluorescens* is one organism known to expresses an α4β4 pyruvate carboxylase. The metabolically engineered cell of the invention therefore is preferably one that has been transformed with a nucleic acid fragment isolated from *P. fluorescens* which contains a nucleotide sequence encoding a pyruvate carboxylase expressed therein, more preferably the pyruvate carboxylase isolated and described in S. Mildrad de Forchetti et al., *J. Gen. Microbiol.*, 93, 75–81 (1976), which is incorporated herein by reference, in its entirety.

Accordingly, the invention also includes a nucleic acid fragment isolated from *P. fluorescens* which includes a nucleotide sequence encoding a pyruvate carboxylase, more preferably a nucleotide sequence that encodes the pyruvate carboxylase isolated and described in S. Mildrad Forchetti et al., *J. Gen. Microbiol.*, 93, 75–81 (1976).

The metabolically engineered cell of the invention is made by transforming a host cell with a nucleic acid fragment comprising a nucleotide sequence encoding an enzyme having pyruvate carboxylase activity. Methods of transformation for bacteria, plant, and animal cells are well known in the art. Common bacterial transformation methods include electroporation and chemical modification. Transformation yields a metabolically engineered cell that overexpresses pyruvate carboxylase. The preferred cells and pyruvate carboxylase enzymes are as described above in connection with the metabolically engineered cell of the invention. Optionally, the cells are further transformed with a nucleic acid fragment comprising a nucleotide sequence encoding an enzyme having PEP carboxylase activity to yield a metabolically engineered cell that also overexpresses pyruvate carboxylase, also as described above. The invention is to be broadly understood as including methods of making the various embodiments of the metabolically engineered cells of the invention described herein.

Preferably, the nucleic acid fragment is introduced into the cell using a vector, although "naked DNA" can also be used. The nucleic acid fragment can be circular or linear, single-stranded or double stranded, and can be DNA, RNA, or any modification or combination thereof. The vector can be a plasmid, a viral vector or a cosmid. Selection of a vector or plasmid backbone depends upon a variety of desired characteristics in the resulting construct, such as a selection marker, plasmid reproduction rate, and the like. Suitable plasmids for expression in *E. coli*, for example, include pUC(X), pKK223-3, pKK233-2, pTrc99A, and pET-(X) wherein (X) denotes a vector family in which numerous constructs are available. pUC(X) vectors can be obtained from Pharmacia Biotech (Piscataway, N.H.) or Sigma Chemical Co. (St. Louis, Mo.). pKK223-3, pKK233-2 and pTrc99A can be obtained from Pharmacia Biotech. pET-(X) vectors can be obtained from Promega (Madison, Wis.), Stratagene (La Jolla, Calif.) and Novagen (Madison, Wis.). To facilitate replication inside a host cell, the vector preferably includes an origin of replication (known as an "ori") or replicon. For example, ColE1 and P15A replicons are commonly used in plasmids that are to be propagated in *E. coli*.

The nucleic acid fragment used to transform the cell according to the invention can optionally include a promoter sequence operably linked to the nucleotide sequence encoding the enzyme to be expressed in the host cell. A promoter is a DNA fragment which causes transcription of genetic material. Transcription is the formation of an RNA chain in accordance with the genetic information contained in the DNA. The invention is not limited by the use of any particular promoter, and a wide variety are known. Promoters act as regulatory signals that bind RNA polymerase in a cell to initiate transcription of a downstream (3' direction) coding sequence. A promoter is "operably linked" to a nucleic acid sequence if it is does, or can be used to, control or regulate transcription of that nucleic acid sequence. The promoter used in the invention can be a constitutive or an inducible promoter. It can be, but need not be, heterologous with respect to the host cell. Preferred promoters for bacterial transformation include lac, lacUV5, tac, trc, T7, SP6 and ara.

The nucleic acid fragment used to transform the host cell can, optionally, include a Shine Dalgarno site (e.g., a ribosome binding site) and a start site (e.g., the codon ATG) to initiate translation of the transcribed message to produce the enzyme. It can, also optionally, include a termination sequence to end translation. A termination sequence is typically a codon for which there exists no corresponding aminoacetyl-tRNA, thus ending polypeptide synthesis. The nucleic acid fragment used to transform the host cell can optionally further include a transcription termination sequence. The rrnB terminators, which is a stretch of DNA that contains two terminators, T1 and T2, is the most commonly used terminator that is incorporated into bacterial expression systems (J. Brosius et al., *J. Mol. Biol.*, 148, 107–127 (1981)).

The nucleic acid fragment used to transform the host cell optionally includes one or more marker sequences, which typically encode a gene product, usually an enzyme, that inactivates or otherwise detects or is detected by a compound in the growth medium. For example, the inclusion of a marker sequence can render the transformed cell resistant to an antibiotic, or it can confer compound-specific metabolism on the transformed cell. Examples of a marker sequence are sequences that confer resistance to kanamycin, ampicillin, chloramphenicol and tetracycline.

Pyruvate carboxylase can be expressed in the host cell from an expression vector containing a nucleic acid fragment comprising the nucleotide sequence encoding the pyruvate carboxylase. Alternatively, the nucleic acid fragment comprising the nucleotide sequence encoding pyruvate carboxylase can be integrated into the host's chromosome. Nucleic acid sequences, whether heterologous or endogenous with respect to the host cell, can be introduced into a bacterial chromosome using, for example, homologous recombination. First, the gene of interest and a gene encoding a drug resistance marker are inserted into a plasmid that contains piece of DNA that is homologous to the region of the chromosome within which the gene of interest is to be inserted. Next this recombinagenic DNA is introduced into the bacteria, and clones are selected in which the DNA fragment containing the gene of interest and drug resistant marker has recombined into the chromosome at the desired location. The gene and drug resistant marker can be introduced into the bacteria via transformation either as a linearized piece of DNA that has been prepared from any cloning vector, or as part of a specialized recombinant suicide vector that cannot replicate in the bacterial host. In the case of linearized DNA, a recD$^-$ host can be used to increase the frequency at which the desired recombinants are obtained. Clones are then verified using PCR and primers that amplify DNA across the region of insertion. PCR products from non-recombinant clones will be smaller in size and only contain the region of the chromosome where the insertion event was to take place, while PCR products from the recombinant clones will be larger in size and contain the region of the chromosome plus the inserted gene and drug resistance.

In a preferred embodiment, the host cell, preferably *E. coli, C. glutamicum, B. flavum* or *B. lactofermentum*, is transformed with a nucleic acid fragment comprising a pyruvate carboxylase gene, preferably a gene that is isolated from *R. etli* or *P. fluorescens*, more preferably the pyc gene from *R. etli*, such that the gene is transcribed and expressed in the host cell to cause increased production of oxaloacetate and, consequently, increased production of the downstream metabolite of interest, relative to a comparable wild-type cell.

The metabolically engineered cell of the invention overexpresses pyruvate carboxylase. Stated in another way, the metabolically engineered cell expresses pyruvate carboxylase at a level higher than the level of pyruvate carboxylase expressed in a comparable wild-type cell. This comparison can be made in any number of ways by one of skill in the art and is done under comparable growth conditions. For example, pyruvate carboxylase activity can be quantified and compared using the method of Payne and Morris (*J. Gen. Microbiol.*, 59, 97–101 (1969)). The metabolically engineered cell that overexpresses pyruvate carboxylase will yield a greater activity than a wild-type cell in this assay. In addition, or alternatively, the amount of pyruvate carboxylase can be quantified and compared by preparing protein extracts from the cells, subjecting them to SDS-PAGE, transferring them to a Western blot, then detecting the biotinylated pyruvate carboxylase protein using detection kits which are commercial available from, for example, Pierce Chemical Company (Rockford, Ill.), Sigma Chemical Company (St. Louis, Mo.) or Boehringer Mannheim (Indianapolis, Ind.) for visualizing biotinylated proteins on Western blots. In some suitable host cells, pyruvate carboxylase expression in the non-engineered, wild-type cell may be below detectable levels.

Optionally, the metabolically engineered cell of the invention also overexpresses PEP carboxylase. In other words, the metabolically engineered cell optionally expresses PEP carboxylase at a level higher than the level of PEP carboxylase expressed in a comparable wild-type cell. Again, this comparison can be made in any number of ways by one of skill in the art and is done under comparable growth conditions. For example, PEP carboxylase activity can be assayed, quantified and compared. In one assay, PEP carboxylase activity is measured in the absence of ATP using PEP instead of pyruvate as the substrate, by monitoring the appearance of CoA-dependent thionitrobenzoate formation at 412 nm (see Example III). The metabolically engineered cell that overexpresses PEP carboxylase will yield a greater PEP carboxylase activity than a wild-type cell. In addition, or alternatively, the amount of PEP carboxylase can be quantified and compared by preparing protein extracts from the cells, subjecting them to SDS-PAGE, transferring them to a Western blot, then detecting the PEP carboxylase protein using PEP antibodies in conjunction with detection kits available from Pierce Chemical Company (Rockford Ill.), Sigma Chemical Company (St. Louis, Mo.) or Boehringer Mannheim (Indianapolis, Ind.) for visualizing antigen-antibody complexes on Western blots. In a preferred embodiment, the metabolically engineered cell expresses PEP carboxylase derived from a cyanobacterium, more preferably Anacystis nidulans.

The invention further includes a method for producing an oxaloacetate-derived biochemical by enhancing or augmenting production of the biochemical in a cell that is, prior to transformation as described herein, capable of biosynthesizing the biochemical. The cell is transformed with a nucleic acid fragment comprising a nucleotide sequence encoding an enzyme having pyruvate carboxylase activity, the enzyme is expressed in the cell so as to cause increased production of the biochemical relative to a comparable, wild-type cell, and the biochemical is isolated from the cell according to known methods. The biochemicals can be isolated from the metabolically engineered cells using protocols, methods and techniques that are well-known in the art. For example, succinic acid can be isolated by electrodialysis (D. Glassner et al., U.S. Pat. No. 5,143,834 (1992)) or by precipitation as calcium succinate (R. Datta, U.S. Pat. No. 5,143,833 (1992)); malic acid can be isolated by electrodialysis (R. Sieipenbusch, U.S. Pat. No. 4,874,700 (1989)); lysine can be isolated by adsorption/reverse osmosis (T. Kaneko et al., U.S. Pat. No. 4,601,829 (1986)). The preferred host cells, oxaloacetate-derived biochemicals, and pyruvate carboxylase enzymes are as described herein.

The biochemicals that are produced or overproduced in, and isolated from, the metabolically engineered cells. according to the method of the invention are those that are or can be metabolically derived from oxaloacetate (i.e., with respect to which oxaloacetate is a metabolic precursor). These oxaloacetate-derived biochemicals include, but are not limited to, amino acids such as lysine, asparagine, aspartate, methionine, threonine, arginine, glutamate, glutamine, proline and isoleucine; organic acids such as succinate, malate, citrate, isocitrate, α-ketoglutarate, succinyl-CoA and fumarate; pyrimidine nucleotides; and porphyrins such as cytochromes, hemoglobins, chlorophylls, and the like. It is to be understood that the terms used herein to describe acids (for example, the terms succinate, aspartate, glutamate, malate, fumarate, and the like) are not meant to denote any particular ionization state of the acid, and are meant to include both protonated and unprotonated forms of the compound. For example, the terms aspartate and aspartic acid refer to the same compound and are used interchangeably, as well as succinate and succinic acid, malate and malic acid, fumarate and fumaric acid, and so on. As is well-known in the art, the protonation state of the acid depends on the $pK_a$ of the acidic group and the pH of the medium. At neutral pH, the acids described herein are typically unprotonated. Additionally, an oxaloacetate-derived biochemical includes a salt of the biochemical. The term succinate, for example, includes succinate salts such as potassium succinate, diammonium succinate, and sodium succinate.

In a particularly preferred method, lysine and succinate are produced in and obtained from a metabolically engineered bacterial cell that expresses pyruvate carboxylase, preferably pyruvate carboxylase derived from either R. etli or P. fluorescens. The method of the invention is to be broadly understood to include the production and isolation of any or all oxaloacetate-derived biochemicals recovered or recoverable from the metabolically engineered cells of the invention, regardless of whether the biochemicals are actually synthesized from oxaloacetate in accordance with the metabolic pathways shown in FIGS. 1–3 or any other presently known metabolic pathways.

Advantages of the invention are illustrated by the following examples. However, the particular materials and amounts thereof recited in these examples, as well as other conditions and details, are to be interpreted to apply broadly in the art and should not be construed to unduly restrict or limit the invention in any way.

EXAMPLE 1

Expression of the R. etli Pyruvate Carboxylase Enzyme Enables E. coli to Convert Pyruvate to Oxaloacetate Materials and Methods Bacterial strains, plasmids and growth conditions. The bacterial strains and plasmids used in this study are listed in Table 1. E. coli strains were grown in LB Miller broth (rich) or M9 minimal media (J. Miller, Experiments in Molecular Genetics, Cold Spring Harbor Laboratory, Cold Spring Harbor, N.Y. (1972)). Strains carrying a plasmid were supplemented with the appropriate antibiotic to detect the marker gene; ampicillin was used at 100 μg/ml in rich media and 50 μg/ml in minimal media while chloramphenicol was used at 20 μg/ml in rich media and 10 μg/ml in minimal media. When isopropyl β-D-thiogalactopyranoside (IPTG) was used to induce the pUC18-pyc construct, it was added at a final concentration of 1 mM.

TABLE 1

Strains and Plasmids

| Strains | Genotype | Reference or source |
|---|---|---|
| MC1061 | araD139 Δ(araABOIC-leu)7679 Δ(lac)74 ga/U ga/K rpsL hsr hsm+ | M. Casadaban et al., J. Mol. Biol., 138, 179–207 (1980) |
| ALS225 | MC1061 FlacIq1 Z+Y+A+ | E. Altman, University of Georgia |
| MG1665 | wt | M. Guyer et al., Quant. Biol., Cold Spring Harbor Symp., 45, 135–140 (1981) |
| JCL 1242 | Δ(argF-lac)U169 ppc::Kn | P. Chao et al., Appl. Env. Microbiol., 59, 4261–4265 (1993) |

| Plasmids | Relevant Characteristics | Reference or source |
|---|---|---|
| pUC18 | Amp(R), ColE1 ori | J. Norrander et al., Gene 26 101–106 (1983) |
| pPC1 | Tet(R), pyc | M. Dunn et al., J. Bacteriol., 178, 5960–5970 (1996) |
| pUC18-pyc | Amp(R), pyc regulated by Plac, ColE1 ori | This example |

TABLE 1-continued

Strains and Plasmids

| pBA11 | Cam(R), birA, P15A ori | D. Barker et al., J. Mol. Biol., 146, 469–492 (1981) |

Construction of pUC18-pyc. The *R. etli* pyc gene, which encodes pyruvate carboxylase, was amplified using the polymerase chain reaction (PCR). Pfu polymerase (Stratagene, La Jolla, Calif.) was used instead of Taq polymerase and the pPC1 plasmid served as the DNA template. Primers were designed based on the published pyc gene sequence (M. Dunn et al., *J. Bacteriol.*, 178 5960–5970 (1996)) to convert the pyc translational start signals to match those of the lacZ gene. These primers also introduced a KpnI (GGTACC) restriction site at the beginning of the amplified fragment and a BglII (AGATCT) restriction site at the end of the amplified fragment; forward primer 5' TAC TAT GGTACC TTA GGA AAC AGC TAT GCC CAT ATC CAA GAT ACT CGT T 3' (SEQ ID NO:1), reverse primer 5' ATT CGT ACT CAG GAT CTG AAA GATCTA ACA GCC TGA CTT TAC ACA ATC G 3' (SEQ ID NO:2) (the KpnI, Shine Dalgarno, ATG start, and BglII sites are underlined). The resulting 3.5 kb fragment was gel isolated, restricted with KpnI and BglII and then ligated into gel isolated pUC18 DNA which had been restricted with KpnI and BamHI to form the pUC18-pyc construct. This construct, identified as "Plasmid in *E. coli* ALS225 pUC18-pyc", was deposited with the American Type Culture Collection (ATCC), 10801 University Blvd., Manassas, Va., 20110-2209, USA, and assigned ATCC number 207111. The deposit was received by the ATCC on Feb. 16, 1999.

Protein gels and Western blotting. Heat-denatured cell extracts were separated on 10% SDS-PAGE gels as per Altman et. al. (*J. Bact.*, 155, 1130–1137 (1983)) and Western blots were carried out as per Carroll and Gherardini (*Infect. Immun.*, 64, 392–398 (1996)). ALS225 *E. coli* cells containing either pUC18 or pUC18-pyc were grown to mid-log in rich media at 37° C. both in the presence and absence of IPTG. Because ALS225 contains lacIq1 on the F', significant induction of the pUC18-pyc construct should not occur unless IPTG is added. Protein extracts were prepared, subjected to SDS PAGE, and Western blotted. Proteins which had been biotinylated in vivo were then detected using the Sigma-Blot protein detection kit (Sigma Chemical Corp., St. Louis, Mo.). The instructions of the manufacturer were followed except that during the development of the western blots the protein biotinylation step was omitted, thus allowing for the detection of only those proteins which had been biotinylated in vivo.

Pyruvate carboxylase (PC) enzyme assay. For pyruvate carboxylase activity measurements, 100 mL of mid-log phase culture was harvested by centrifugation at 7,000×g for 15 minutes at 4° C. and washed with 10 mL of 100 mM Tris-Cl (pH 8.0). The cells were then resuspended in 4 mL of 100 mM Tris-Cl (pH 8.0) and subsequently subjected to cell disruption by sonication. The cell debris was removed by centrifugation at 20,000×g for 15 minutes at 4° C. The pyruvate carboxylase activity was measured by the method of Payne and Morris (*J. Gen. Microbiol.*, 59, 97–101 (1969)). In this assay the oxaloacetate produced by pyruvate carboxylase is converted to citrate by the addition of citrate synthase in the presence of acetyl CoA and 5,5-dithio-bis (2-nitro-benzoate) (DTNB) (Aldrich Chemical Co.); the homotetramer pyruvate carboxylase enzyme from *R. etli* requires acetyl coenzyme A for activation. The rate of increase in absorbence at 412 nm due to the presence of CoA-dependent formation of the 5-thio-2-nitrobenzoate was monitored, first after the addition of pyruvate and then after the addition of ATP. The difference between these two rates was taken as the ATP-dependent pyruvate carboxylase activity. The concentration of reaction components per milliliter of mixture was as follows: 100 mM Tris-Cl (pH 8.0), 5 mM $MgCl_2.H_2O$, 50 mM Na $HCO_3$, 0.1 mM acetyl CoA, 0.25 mM DTNB, and 5 units (U) of citrate synthase. Pyruvate, ATP, ADP, or aspartate, were added as specified in the Results section, below. The reaction was started by adding 50 μl of cell extract. One unit of pyruvate carboxylase activity corresponds to the formation of 1 μmol of 5-thio-2-nitrobenzoate per mg of protein per minute. All enzyme assays were performed in triplicate and a standard error of less then 10% was observed. The total protein in the cell extracts was determined by the Lowry method (O. Lowry et al., *J. Biol. Chem.*, 193, 265–275 (1951)).

Results

Expression of the *R. etli* pyruvate carboxylase enzyme in *E. coli*. The *R. etli* pyc gene, which encodes pyruvate carboxylase, was PCR amplified from pPC1 and subcloned into the pUC18 cloning/expression vector as described above. Because the translational start signals of the *R. etli* pyc gene were nonoptimal (pyc from *R. etli* uses the rare TTA start codon as well as a short spacing distance between the Shine Dalgarno and the start codon), the translational start signals were converted to match that of the lacZ gene which can be expressed at high levels in *E. coli* using a variety of expression vectors. When induced cell extracts of the pUC18-pyc construct were assayed via western blots developed to detect biotinylated proteins, a band of about 120 kD was detected. This value is consistent with the previously reported size assessment for the *R. etli* pyruvate carboxylase enzyme (M. Dunn et al., *J. Bacteriol.*, 178, 5960–5970 (1996)). By comparing serial dilutions of the pyruvate carboxylase which was expressed from the pUC18-pyc construct with purified pyruvate carboxylase enzyme obtained commercially, it was determined that, under fully induced conditions pyruvate carboxylase from *R. etli* was being expressed at 1% of total cellular protein in *E. coli*.

Effects of biotin and biotin holoenzyme synthase on the expression of biotinylated *R. etli* pyruvate carboxylase in *E. coli*. Pyruvate carboxylase is a biotin-dependent enzyme, and mediates the formation of oxaloacetate by a two-step carboxylation of pyruvate. In the first reaction step, biotin is carboxylated with ATP and bicarbonate as substrates, while in the second reaction the carboxyl group from carboxybiotin is transferred to pyruvate. All pyruvate carboxylases studied to date have been found to be biotin-dependent and exist as multimeric proteins, but the size and structure of the associated subunits can vary considerably. Pyruvate carboxylases from different bacteria have been shown to form $\alpha_4$, or $\alpha_4\beta_4$ structures with the size of the α subunit ranging from 65 to 130 kD. In all cases, however, the a subunit of the pyruvate carboxylase enzyme has been shown to contain three catalytic domains—a biotin carboxylase domain, a transcarboxylase domain, and a biotin carboxyl carrier protein domain—which work collectively to catalyze the two-step conversion of pyruvate to oxaloacetate. In the first step, a biotin prosthetic group linked to a lysine residue is carboxylated with ATP and $HCO_3^-$, while in the second step, the carboxyl group is transferred to pyruvate. The biotinylation of pyruvate carboxylase occurs post-translationally and is catalyzed by the enzyme biotin holoenzyme synthase. In this experiment, *E. coli* cells containing the pUC18-pyc construct were grown under inducing conditions in minimal defined media which either contained no added biotin, or biotin added at 50 or 100 ng/mL. Specifically, MG1655 pUC18-pyc cells were grown to mid-log at 37° C. in M9 media that contained varying amounts of biotin. Protein extracts were prepared, subjected to SDS PAGE, and Western blotted. Proteins which had been biotinylated in vivo were then detected using the Sigma-Blot protein detection kit, as described above. MG1655 was used in this experiment because it grows significantly faster than ALS225 in minimal media. Because MG1655 does not contain lacIq1, maximal expression of pyruvate carboxylase could be achieved without adding IPTG. The amount of biotinylated pyruvate carboxylase that was present in each sample was quantitated using a Stratagene Eagle Eye II Still Video. The biotinylation of pyruvate carboxylase that was expressed from the pUC18-pyc construct was clearly affected by biotin levels. Cells that had to produce all their biotin de novo expressed significantly lower amounts of biotinylated protein. The addition of biotin at a final concentration of 50 ng/mL was sufficient to biotinylate all of the pyruvate carboxylase that was expressed via the pUC18-pyc construct.

Since the post-translational biotinylation of pyruvate carboxylase is carried out by the enzyme biotin holoenzyme synthase, the effect of excess biotin holoenzyme synthase on the biotinylation of pyruvate carboxylase was investigated. This analysis was accomplished by introducing the multicopy plasmid pBA11 (which contains the birA gene encoding biotin holoenzyme synthase) into $E.$ $coli$ cells that also harbored the pUC18-pyc construct; pBA11 is a pACYC184 derivative and thus compatible with pUC18-pyc. The effects of excess biotin holoenzyme synthase enzyme were examined in rich media where biotin would also be present in excess. Specifically, ALS225 cells containing pUC18-pyc, or pBA11 were grown to mid-log at 37° C. in rich media that contained IPTG. Protein extracts were prepared, subjected to SDS PAGE, and Western blotted, and proteins which had been biotinylated in vivo were then detected using the Sigma-Blot protein detection kit as described above. Barker et al. (J. Mol. Biol., 146, 469–492 (1981)) have shown that pBA11 causes a 12-fold increase in biotin holoenzyme synthase enzyme levels. The amount of biotinylated pyruvate carboxylase that was present in each sample was quantitated using a Stratagene Eagle Eye II Still Video System. Protein extracts prepared from cells which either contained only pUC18-pyc or both pUC18-pyc and pBA11 yielded equal amounts of biotinylated pyruvate carboxylase protein. This result suggests that a single chromosomal copy of birA is sufficient to biotinylate all of the pyruvate carboxylase that is expressed when biotin is present in excess.

Figure 5:
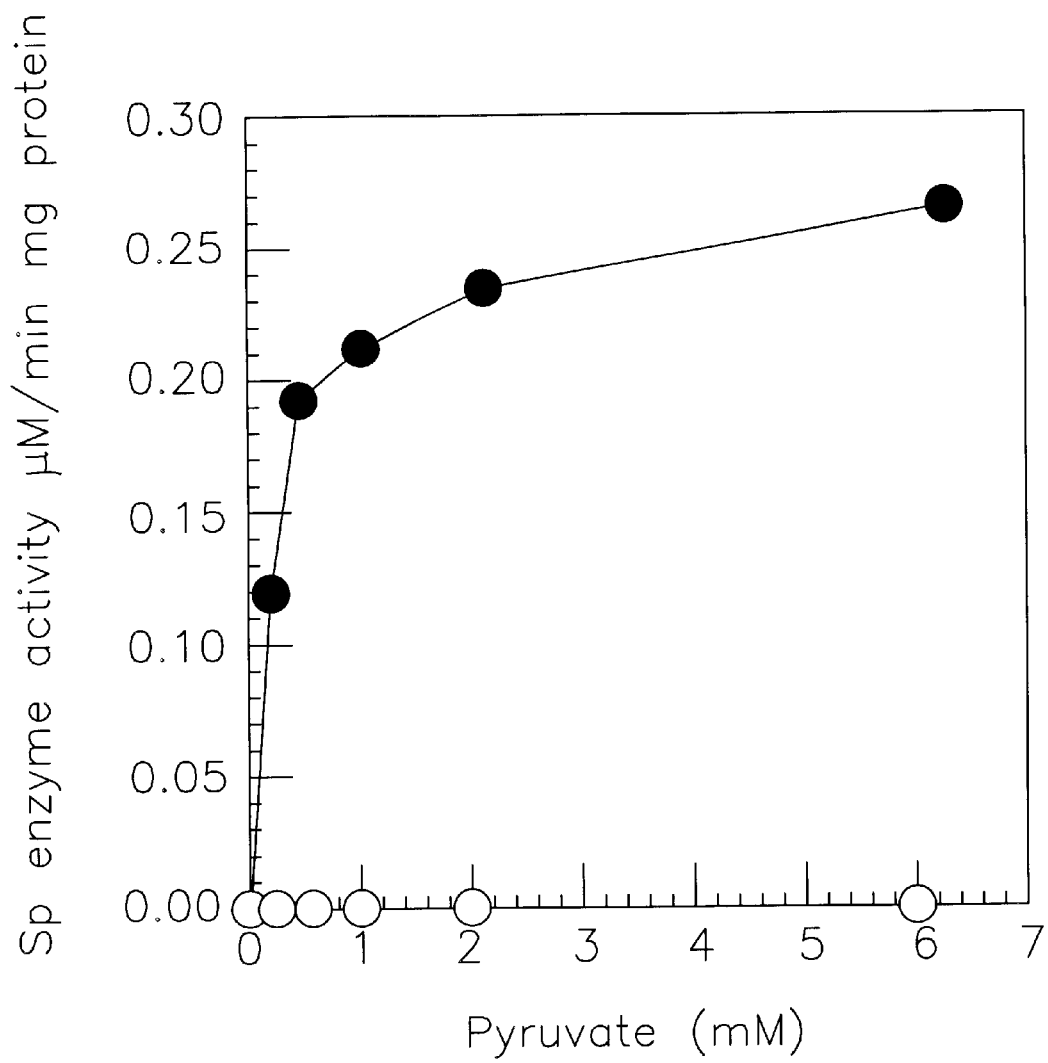
FIG. 5. Kinetic analysis of pyruvate carboxylase activities for MG1655 pUC18 (○) and MG1655 pUC18-pyc (●) with respect to pyruvate.

R. etli pyruvate carboxylase can convert pyruvate to oxaloacetate in $E.$ $coli$. To confirm that the expressed pyruvate carboxylase protein was enzymatically active in $E.$ $coli$, the coupled enzyme assay developed by Payne and Morris was employed to assess pyruvate carboxylase activity (J. Payne et al., J. Gen. Microbiol., 59, 97–101 (1969)). Cell extracts containing the induced pUC18-pyc construct (MG1655 pUC18-pyc) were tested for pyruvate carboxylase activity using varying amounts of pyruvate, and compared to controls containing the pUC18 construct (MG1655 pUC18). ATP was added at a final concentration of 5 mM to the reaction mixture and pyruvate carboxylase activity was determined in the presence of increasing amounts of pyruvate. FIG. 5 shows that $E.$ $coli$ cells harboring the pUC18-pyc construct could indeed convert pyruvate to oxaloacetate and that the observed pyruvate carboxylase activity followed Michaelis-Menten kinetics. A Lineweaver-Burke plot of these data revealed that the saturation constant ($K_m$) for expressed pyruvate carboxylase was 0.249 mM with respect to pyruvate. This value is in excellent agreement with other pyruvate carboxylase enzymes that have been studied (H. Feir et al., Can. J. Biochem., 47, 698–710 (1969); H. Modak et al., Microbiol., 141, 2619–2628 (1995); M. Scrutton et al., Arch. Biochem. Biophys., 164, 641–654 (1974)).

Figure 6:
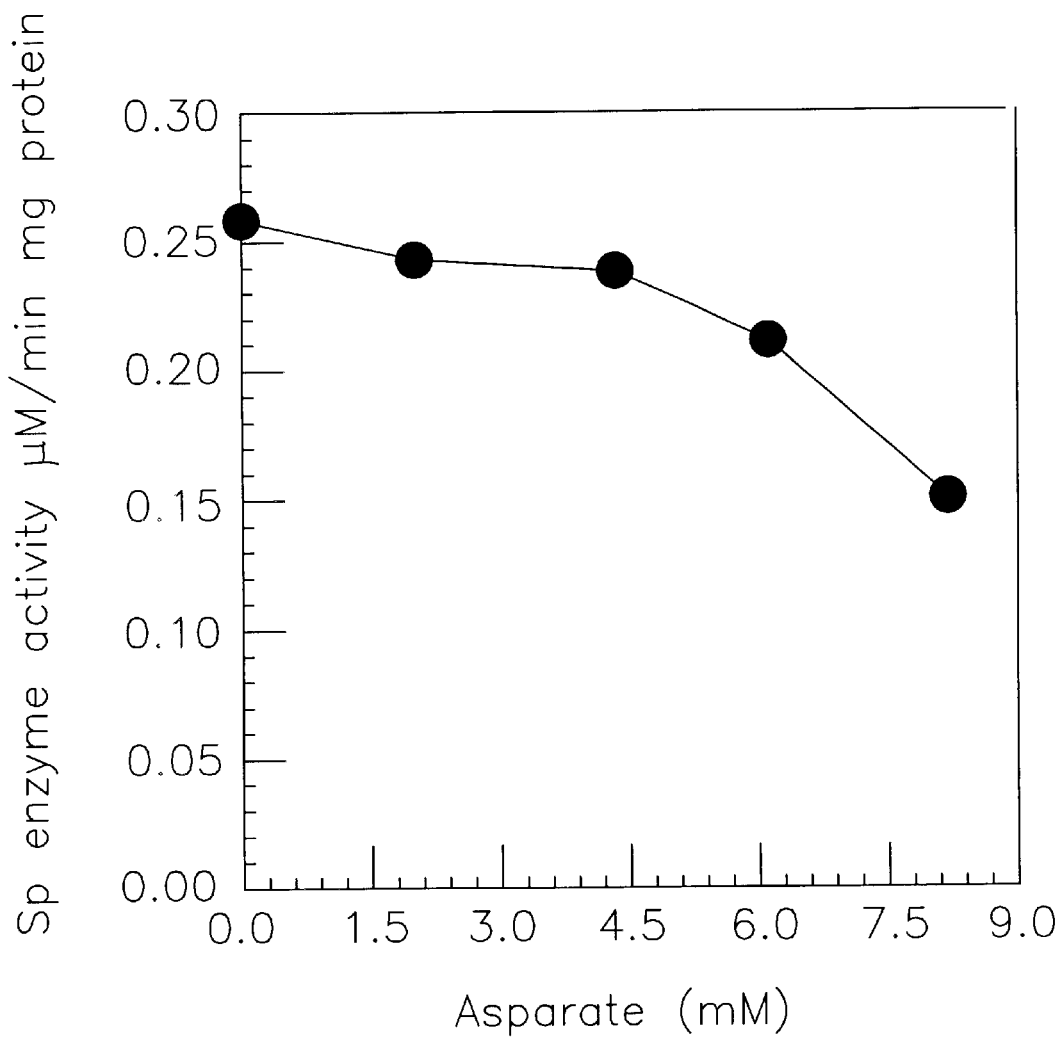
FIG. 6. Effects of increasing aspartate concentrations on the activity of pyruvate carboxylase.
Figure 7:
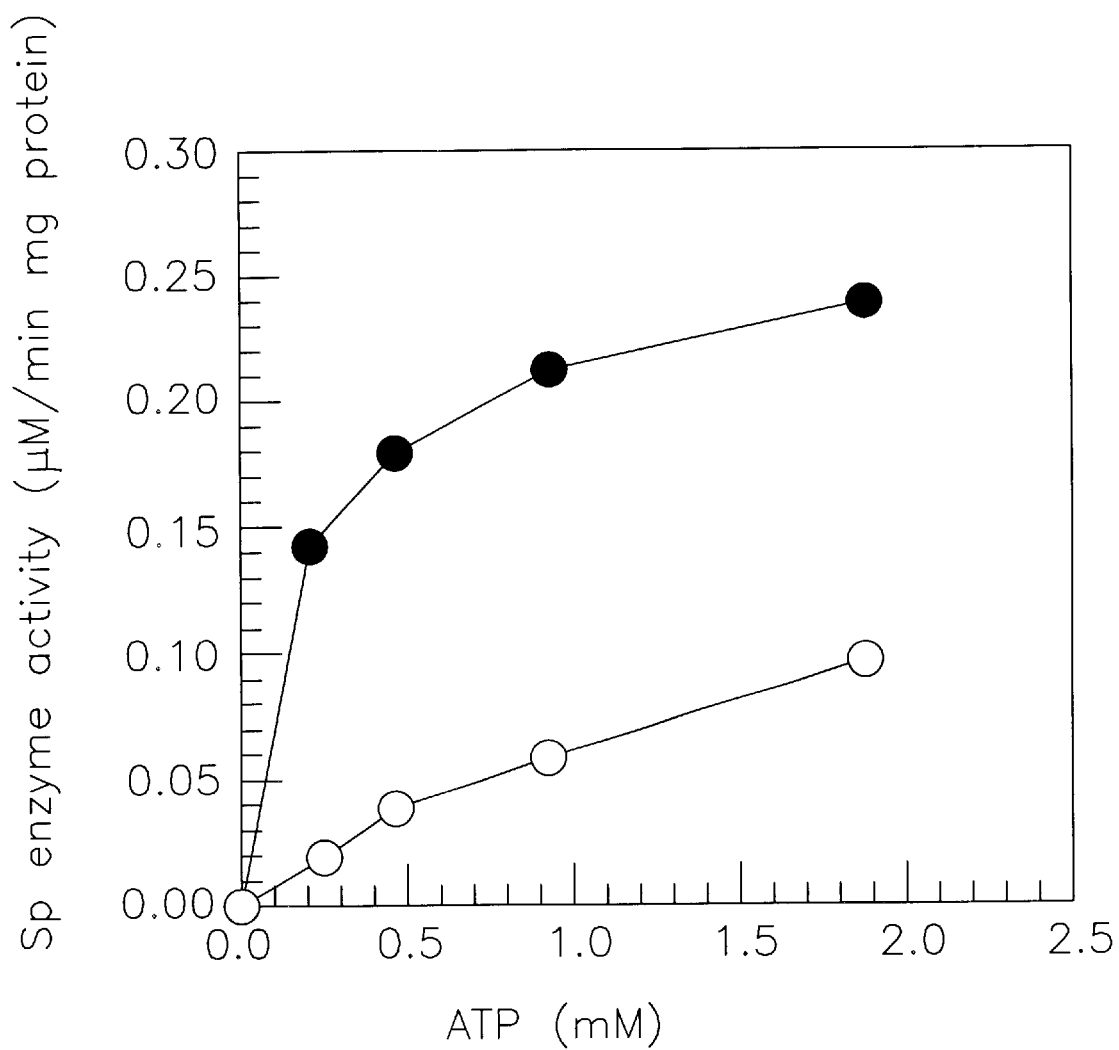
FIG. 7. Kinetic analysis of pyruvate carboxylase with respect to ATP and ADP; pyruvate carboxylase activity was determined in the absence of ADP (●) and in the presence of 1.5 mM ADP (○).

It is well documented that the α4 pyruvate carboxylase enzymes can be inhibited by either aspartate or adenosine diphosphate (ADP). Aspartate is the first amino acid that is synthesized from oxaloacetate and ADP is liberated when pyruvate carboxylase converts pyruvate to oxaloacetate. Pyruvate carboxylase activity in the presence of each of these inhibitors was evaluated using extracts of MG1655 cells that contained the pUC18-pyc construct. The effect of aspartate was analyzed by adding ATP and pyruvate to the reaction mixture to final concentrations of 5 mM and 6 mM, respectively, then determining pyruvate carboxylase activity in the presence of increasing amounts of aspartate. FIG. 6 shows the pyruvate carboxylase activity that was obtained in the presence of different concentrations of aspartate. As expected, the pyruvate carboxylase activity was inhibited by aspartate and the specific activity decreased to approximately 43% in the presence of 8 mM aspartate. The effect of ADP was analyzed by adding pyruvate to the reaction mixture to a final concentration of 5 mM, then determining pyruvate carboxylase activity in the presence of increasing amounts of ATP. FIG. 7 shows that ADP severely affected the observed pyruvate carboxylase activity and acted as a competitive inhibitor of ATP. A Lineweaver-Burke plot of these data revealed that the saturation constant ($K_m$) for expressed pyruvate carboxylase was 0.193 mM with respect to ATP and that the inhibition constant for ADP was 0.142 mM. Again, these values were in excellent agreement with other pyruvate carboxylase enzymes that have been studied H. Feir et al., Can. J. Biochem., 47, 697–710 (1969); H. Modak et al., Microbiol., 141, 2619–2628 (1995); M. Scrutton et al., Arch. Biochem. Biophys., 164, 641–654 (1974)).

Figure 8:
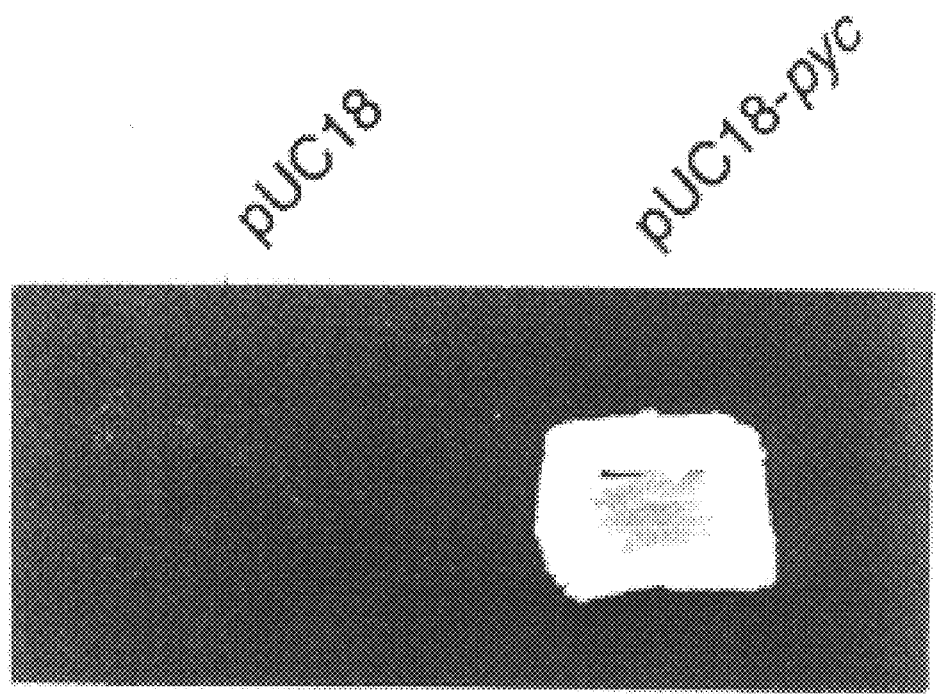
FIG. 8. Growth of a ppc null *E. coli* strain which contains either pUC18 or the pUC18-pyc construct on minimal media that utilizes glucose as a sole carbon source.

To show that the expression of R. etli pyruvate carboxylase in $E.$ $coli$ can truly divert carbon flow from pyruvate to oxaloacetate, we tested whether the pUC18-pyc construct could enable an $E.$ $coli$ strain which contained a ppc null allele (ppc encodes PEP carboxylase) to grow on minimal glucose media. Because $E.$ $coli$ lacks pyruvate carboxylase and thus is only able to synthesize oxaloacetate from PEP, (see FIG. 3) $E.$ $coli$ strains which contain a disrupted ppc gene can not grow on minimal media which utilizes glucose as the sole carbon source (P. Chao et al., Appl. Env. Microbiol., 59, 4261–4265 (1993)). The cell line used for this experiment was JCL1242 (ppc::kan), which contains a kanamycin resistant cassette that has been inserted into the ppc gene and thus does not express the PEP carboxylase enzyme. JCL1242 cells containing either pUC18 or the pUC18-pyc construct were patched onto minimal M9 glucose thiamine ampicillin IPTG plates and incubated at 37° C. for 48 hours. As shown in FIG. 8, $E.$ $coli$ cells which contain both the ppc null allele and the pUC18-pyc construct were able to grow on minimal glucose plates. This complementation demonstrates that a branch point can be created at the level of pyruvate which results in the rerouting of carbon flow towards oxaloacetate, and clearly shows that pyruvate carboxylase is able to divert carbon flow from pyruvate to oxaloacetate in $E.$ $coli$.

EXAMPLE II

Expression of *R. etli* Pyruvate Carboxylase Causes Increased Succinate Production in *E. coli*

Materials and Methods

Bacterial strains and plasmids. The *E. coli* strains used in this study are listed in Table 2. The lactate dehydrogenase mutant strain designated RE02 was derived from MG1655 by P1 phage transduction using *E. coli* strain NZN111 (P. Bunch et al., *Microbiol.*, 143, 187–195 (1997)).

TABLE 2

Strains and plasmids used.

| Strains | Genotype | Reference or Source |
| --- | --- | --- |
| MG1655 | Wild type | M. Guyer et al., Quant. Biol., Cold Spring Harbor Symp., 45, 135–140 (1981) |
| RE02 | MG1655 ldh | This example |
| Plasmids | Relevant Characteristics | Reference or Source |
| pUC18-pyc | Amp(R), pyc regulated by Plac | Example I |
| pTrc99A | Amp(R), lacIq, Ptrc | E. Amann et al., Gene, 69:301–315 (1988) |
| pTrc99A-pyc | Amp(R), lacIq, pyc regulated by Ptrc | This example |

The pyc gene from *R. etli* was originally cloned under the control of the lac promoter (Example I). Because this promoter is subjected to catabolic repression in the presence of glucose, a 3.5 kb XbaI-KpnI fragment from pUC18-pyc was ligated into the pTrc99A expression vector which had been digested with XbaI and KpnI. The new plasmid was designated as pTrc99A-pyc. This plasmid, identified as "Plasmid in *E. coli* ALS225 pTrc99A-pyc", was deposited with the American Type Culture Collection (ATCC), 10801 University Blvd., Manassas, Va., 20110-2209, USA, and assigned ATCC number 207112. The deposit was received by the ATCC on Feb. 16, 1999. In this new construct the transcription of the pyc gene is under the control of artificial trc promoter and thus is not subjected to catabolic repression in the presence of glucose.

Media and growth conditions. For strain construction, *E. coli* strains were grown aerobically in Luria-Bertani (LB) medium. Anaerobic fermentations were carried out in 100 mL serum bottles with 50 mL LB medium supplemented with 20 g/L glucose and 40 g/L $MgCO_3$. The fermentations were terminated at 24 hours at which point the pH values of all fermentations were approximately pH 6.7, and glucose was completely utilized. For plasmid-containing strains either ampicillin or carbenicillin was added to introduce selective pressure during the fermentation. Each of these antibiotics was introduced initially at 100 µg/mL. In one set of experiments, no additional antibiotic was added during fermentation, while in a second set of experiments an additional 50 µg/mL was added at 7 hours and 14 hours. Pyruvate carboxylase was induced by adding 1 mM IPTG. For enzyme assays cells were grown in LB medium supplemented with 20 g/L glucose and buffered with 3.2 g/L $Na_2CO_3$.

Fermentation product analysis and enzyme assays. Glucose, succinate, acetate, formate, lactate, pyruvate and ethanol were analyzed by high-pressure liquid chromatography (HPLC) using a Coregel 64-H ion-exclusion column (Interactive Chromatography, San Jose, Calif.) and a differential refractive index detector (Model 410, Waters, Milford, Mass.). The eluant was 4 mN H2SO4 and the column was maintained at 60° C.

For enzyme activity measurements, 50 mL of mid-log phase culture were harvested by centrifugation (10000×g for 10 minutes at 4° C.) and washed with 10 mL of 100 mM Tris-HCl buffer (pH 8.0). The cells were then resuspended in 2 mL of 100 mM Tris-HCl buffer and subjected to cell disruption by sonication. Cell debris were removed by centrifugation (20000×g for 15 minutes at 4° C.). Pyruvate carboxylase activity (J. Payne et al., *J. Gen. Microbiol.* 59, 97–101 (1969); see also Example I), and the endogenous activities of PEP carboxylase (K. Terada et al., *J. Biochem.*, 109, 49–54 (1991)), malate dehydrogenase and lactate dehydrogenase (P. Bunch et al., *Microbiol.*, 143 187–195 (1997)) were then measured. The total protein in the cell extract was determined using the Lowry method.

Results

Table 3 shows that pyruvate carboxylase activity could be detected when the pTrc99A-pyc construct was introduced into either wild type cells (MG1655) or wild type cells which contained a ldh⁻ null mutation (RE02). The presence of IPTG did not significantly affect the expression of other important metabolic enzymes such as PEP carboxylase, lactate dehydrogenase and malate dehydrogenase.

TABLE 3

Enzyme activity in exponential phase cultures.

| | | Specific activity (µmol/min mg protein) | | | |
| --- | --- | --- | --- | --- | --- |
| Strain | IPRG | Pyruvate carboxylase | PEP carboxylase | Lactate dehydrogenase | Malate dehydrogenase |
| MG1655 | − | 0.00 | 0.15 | 0.31 | 0.06 |
| | + | 0.00 | 0.18 | 0.38 | 0.06 |
| MG1655 pTrc99A-pyc | − | 0.00 | 0.15 | 0.32 | 0.05 |
| | + | 0.22 | 0.11 | 0.32 | 0.05 |
| RE02 | − | 0.00 | 0.15 | 0.00 | 0.04 |
| | + | 0.00 | 0.13 | 0.00 | 0.04 |
| RE02 pTrc99A-pyc | − | 0.00 | 0.15 | 0.00 | 0.04 |
| | + | 0.32 | 0.12 | 0.00 | 0.05 |

In order to elucidate the effect of pyruvate carboxylase expression on the distribution of the fermentation end products, several 50 mL serum bottle fermentations were conducted (see Table 4).

TABLE 4

Effect of pyruvate carboxylase on product distribution from *E. coli* glucose fermentation.

| Strain | Antibiotic | Mode of antibiotic addition | Pyruvate (g/L) | Succinate (g/L) | Lactate (g/L) | Formate (g/L) | Acetate (g/L) | Ethanol (g/L) |
|---|---|---|---|---|---|---|---|---|
| MG1655 (wt) | — | — | 0.00 (0.00) | 1.57 (0.17) | 4.30 (0.73) | 4.34 (0.50) | 3.34 (0.36) | 2.43 (0.24) |
| MG1655 pTrc99A-pyc | Amp | 1x | 0.00 (0.00) | 4.36 (0.45) | 2.22 (0.49) | 3.05 (0.57) | 3.51 (0.03) | 2.27 (0.30) |
| MG1655 pTrc99A-pyc | Car | 1x | 0.00 (0.00) | 4.42 (0.44) | 2.38 (0.76) | 2.94 (0.46) | 3.11 (0.36) | 2.27 (0.30) |
| MG1655 pTrc99A-pyc | Amp | 3x | 0.00 (0.00) | 4.41 (0.07) | 1.65 (0.08) | 4.17 (0.15) | 3.93 (0.11) | 2.91 (0.34) |
| MG1655 pTrc99A-pyc | Car | 3x | 0.00 (0.00) | 4.37 (0.06) | 1.84 (0.07) | 4.09 (0.08) | 3.88 (0.06) | 2.58 (0.09) |
| RE02 (ldh$^-$) | — | — | 0.61 (0.06) | 1.73 (0.12) | 0.00 (0.00) | 6.37 (0.46) | 4.12 (0.30) | 3.10 (0.26) |
| RE02 pTrc99A-pyc | Amp | 1x | 0.33 (0.11) | 2.92 (0.12) | 0.00 (0.00) | 5.38 (0.12) | 4.09 (0.16) | 2.53 (0.03) |
| RE02 pTrc99A-pyc | Car | 1x | 0.25 (0.05) | 2.99 (0.55) | 0.00 (0.00) | 5.50 (0.90) | 4.23 (0.71) | 2.50 (0.44) |
| RE02 pTrc99A-pyc | Amp | 3x | 0.30 (0.04) | 2.74 (0.07) | 0.00 (0.00) | 6.48 (0.04) | 4.75 (0.06) | 2.99 (0.03) |
| RE02 pTrc99A-pyc | Car | 3x | 0.33 (0.04) | 2.65 (0.05) | 0.00 (0.00) | 6.21 (0.18) | 4.60 (0.12) | 3.05 (0.07) |

Antibiotics were either added once at 0 hours at a concentration of 100 µg/mL (1x) or added at 0 hours at a concentration of 100 µg/mL and again at 7 hours and 14 hours at 50 µg/mL (3x). Values are the mean of three replicates and standard deviations are shown in parentheses. To calculate the net yield of each product per gram of glucose consumed, the final product concentration is divided by 20 g/L of glucose.

As shown in Table 4, expression of pyruvate carboxylase caused a significant increase in succinate production in both MG1655 (wild type) and RE02 (ldh$^-$). With MG1655 the induction of pyruvate carboxylase increased the production of succinate 2.7-fold from 1.57 g/L in the control strain to 4.36 g/L, thus making succinate the major product of glucose fermentation. This increase in succinate was accompanied by decreased lactate and formate formation, indicating that carbon was diverted away from lactate toward succinate formation. A similar carbon diversion from lactate toward succinate was achieved previously by the overexpression of native PEP carboxylase (C. Millard et al., *Appl. Environ. Microbiol.*, 62, 1808–1810 (1996)). Table 4 also shows that ampicillin and carbenicillin were equally effective in maintaining sufficient selective pressure, and that the addition of more of either antibiotic during the fermentation did not further enhance the succinate production. This evidence indicates that an initial dose (of 100 µg/mL) is sufficient to maintain selective pressure throughout the fermentation, a result which might be due to the relatively high final pH (6.8) observed in our fermentation studies versus the final pH (6.0) observed in previous studies (C. Millard et al., *Appl. Environ. Microbiol.*, 62, 1808–1810 (1996)).

Because introducing pyruvate carboxylase into *E. coli* was so successful at directing more carbon to the succinate branch, we were also interested in determining whether additional carbon could be directed to succinate by eliminating lactate dehydrogenase, since this enzyme also competes for pyruvate. Table 4 compares the results of fermentations using the RE02 (ldh$^-$) strain with or without the pTrc99A-pyc plasmid. Compared to the wild type strain (MG1655), the RE02 strain showed no significant change in succinate production. Instead, fermentations with the RE02 strain, whether it contained the pTrc99A-pyc plasmid or not, resulted in increased formate, acetate and ethanol production, accompanied by secretion of pyruvate. The fact that pyruvate was secreted into the fermentation broth indicates that the rate of glycolysis was greater than the rate of pyruvate utilization. The observed increase in formate concentrations in the ldh$^-$ mutant may be caused by the accumulation of pyruvate, a compound which is known to exert a positive allosteric effect on pyruvate formate lyase (G. Sawers et al., *J. Bacteriol.*, 170, 5330–5336 (1988)). With RE02 the induction of pyruvate carboxylase increased the production of succinate 1.7-fold from 1.73 g/L in the control strain to 2.92 g/L. Thus, the succinate increase obtained in the ldh$^-$ mutant strains was significantly lower than that obtained in the wild type strain (MG1655). A possible explanation for this observation might be that pyruvate carboxylase activity was inhibited by a cellular compound which accumulated in the ldh$^-$ mutants.

Figure 9:
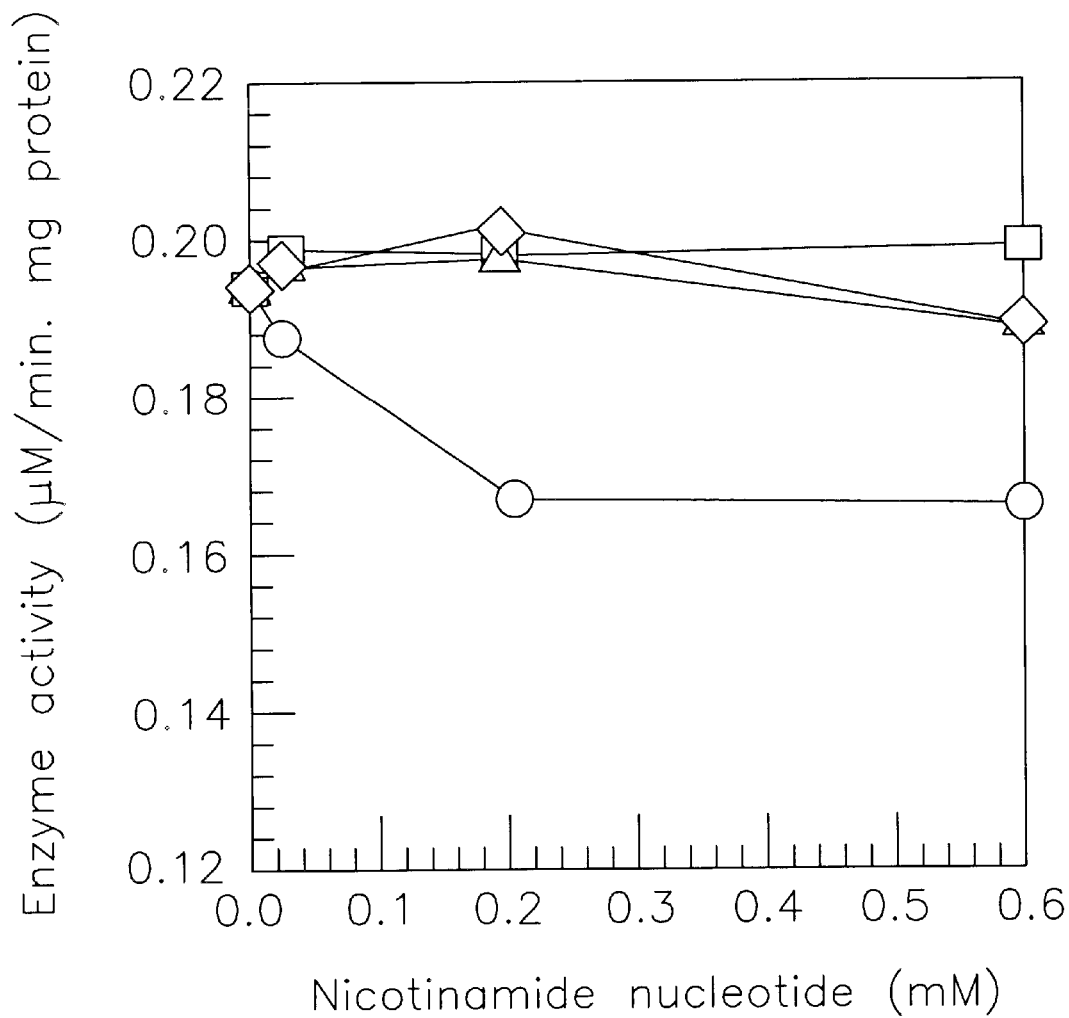
FIG. 9. Effect of nicotinamide nucleotides on pyruvate carboxylase activity: NADH (○), NAD+(□), NADPH (Δ) and NADP+(□).

During glycolysis two moles of reduced nicotinamide adenine dinucleotide (NADM) are generated per mole of glucose. NADH is then oxidized during the formation of ethanol, lactate and succinate under anaerobic conditions. The inability of the ldh$^-$ mutants to consume NADH through lactate formation may put stress on the oxidizing capacity of these strains, leading to an accumulation of NADH. Indeed, this reduced cofactor has previously been shown to inhibit a pyruvate carboxylase isolated from Saccharomyces cerevisiae (J. Cazzulo et al., *Biochem. J.*, 112, 755–762 (1969)). In order to elucidate whether such oxidizing stress might be the cause of the attenuated benefit that was observed when pyruvate carboxylase was expressed in the ldh$^-$ mutants, we investigated the effect of both oxidized and reduced nicotinamide adenine dinucleotide (NADH/NAD+) and dinucleotide phosphate (NADPH/NADP+) on pyruvate carboxylase activity. Enzyme assays were conducted with cell-free crude extract obtained from MG1655 pTrc99A-pyc. All assays were conducted in triplicate, and average values are shown in FIG. 9. Standard deviation was no greater than 5% for all data points. NADH inhibited pyruvate carboxylase, whereas NAD+, NADP+ and NADPH did not. The lower succinate enhancement with RE02 the ldh$^-$ mutant is therefore hypothesized to result from an accumulation of intracellular NADH, a cofactor which appears to inhibit pyruvate carboxylase activity.

EXAMPLE III

Expression of *R. etli* Pyruvate Carboxylase Does Not Affect Glucose Uptake in *E. coli* in Anaerobic Fermentation Methods Microorganisms and plasmids. *E. coli* strain MG1655 (wild type Fλ$^-$; M. Guyer et al., *Quant. Biol.*, Cold Spring Harbor Symp.,45, 135–140 (1980); see also Example I) and the plasmid pUC18-pyc which contains the pyc gene from *R. etli* (see Example I).

Media and fermentation. All 2.0 L fermentations were carried out in 2.5 L New Brunswick Baffle III bench top fermenters (New Brunswick Scientific, Edison, N.J.) in Luria-Bertani (LB) supplemented with glucose, 10 g/L;

Na$_2$PHO$_4$.7H$_2$O, 3 g/L; KH$_2$PO$_4$, 1.5 g/L; NH$_4$Cl, 1 g/L; MgSO$_4$.7H$_2$O, 0.25 g/L; and CaCl$_2$.2H$_2$O, 0.02 g/L. The fermenters were inoculated with 50 mL of anaerobically grown culture. The fermenters were operated at 150 rpm, 0% oxygen saturation (Ingold polarographic oxygen sensor, New Brunswick Scientific, Edison, N.J.), 37° C., and pH 6.4, which was controlled with 10% NaOH. Anaerobic conditions were maintained by flushing the headspace of the fermenter with oxygen-free carbon dioxide. When necessary, the media was supplemented with an initial concentration of 100 μg/mL ampicillin, previously shown to be sufficient to maintain the selective pressure (Example I).

Analytical methods. Cell growth was monitored by measuring the optical density (OD) (DU-650 spectrophotometer, Beckman Instruments, San Jose, Calif.) at 600 nm. This optical density was correlated with dry cell mass using a calibration curve of dry cell mass (g/L)=0.48×OD. Glucose and fermentation products were analyzed by high-pressure liquid chromatography using Coregel 64-H ion-exclusion column (Interactive Chromatography, San Jose, Calif.) as described in Example II.

The activity of pyruvate carboxylase and the endogenous activity of PEP carboxylase was measured by growing each strain and clone separately in 160 mL serum bottles under strict anaerobic conditions. Cultures were harvested in mid-logarithmic growth, washed and subjected to cell disruption by sonication. Cell debris were removed by centrifugation (20000×g for 15 min at 4° C.). Pyruvate carboxylase activity was measured as previously described (Payne and Morris, 1969), and the PEP carboxylase activity was measured in the absence of ATP using PEP instead of pyruvate as the substrate, with the appearance of CoA-dependent thionitrobenzoate formation at 412 nm monitored. The total protein in the cell extract was determined using the Lowry method.

Results

Figure 2:
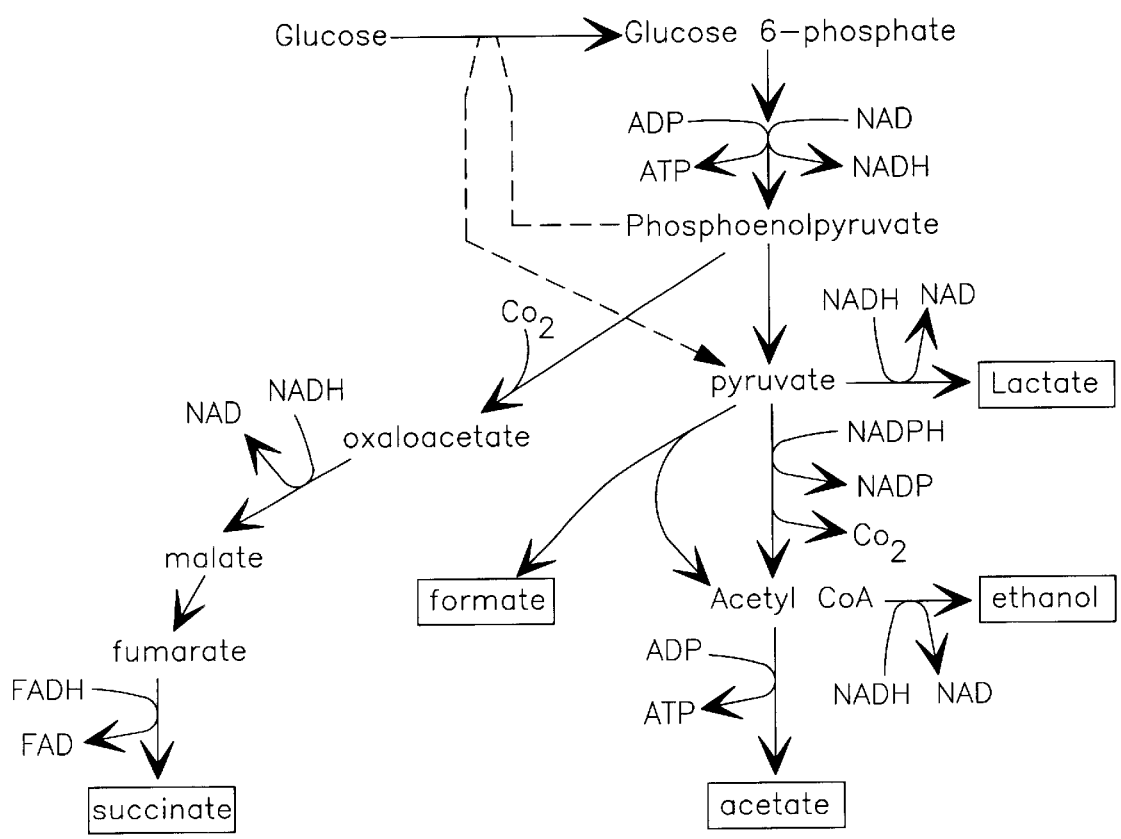
FIG. 2. Anaerobic pathway in *E. coli* depicting glycolysis and biosynthesis of selected oxaloacetate-derived biochemicals; the participation of PEP in glucose uptake is shown by the dashed line; the pathway as shown is not stoichiometric, nor does it include all cofactors.
Figure 3:
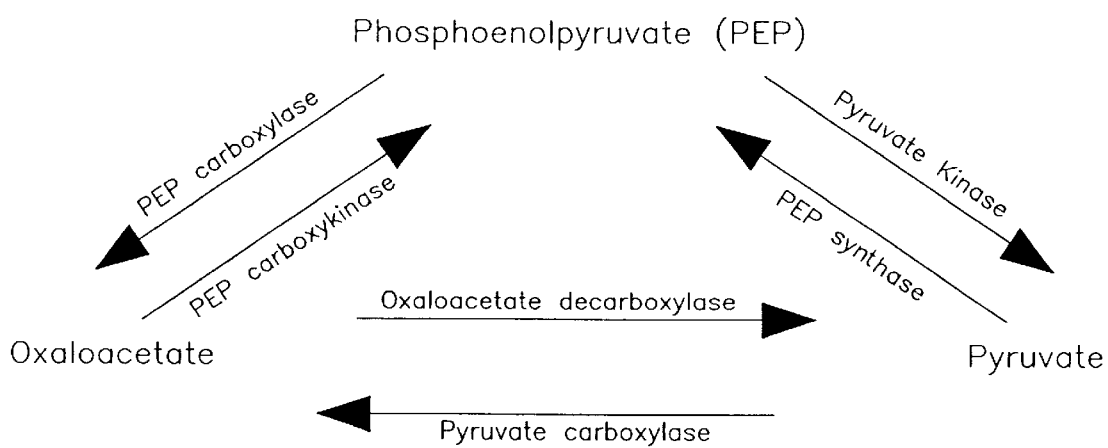
FIG. 3. Biosynthetic pathways that directly regulate the intracellular levels of oxaloacetate; not all organisms contain all of these enzymes; *E. coli*, for example, does not contain pyruvate carboxylase.
Figure 4:
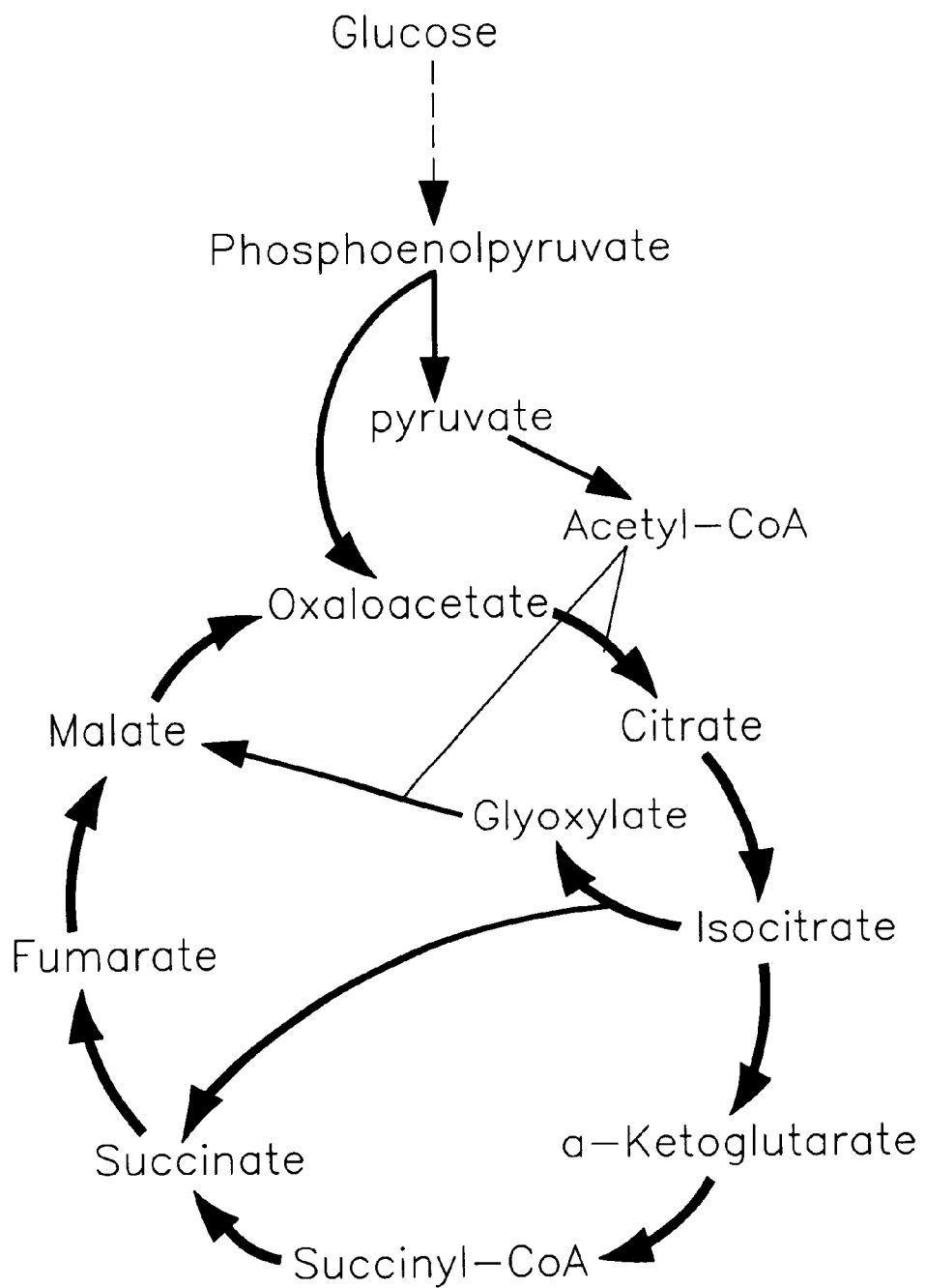
FIG. 4. The TCA cycle, showing entry into the cycle of 3-carbon intermediates and also including the glyoxylate shunt for 2-carbon intermediates (darker arrows).
Figure 10:
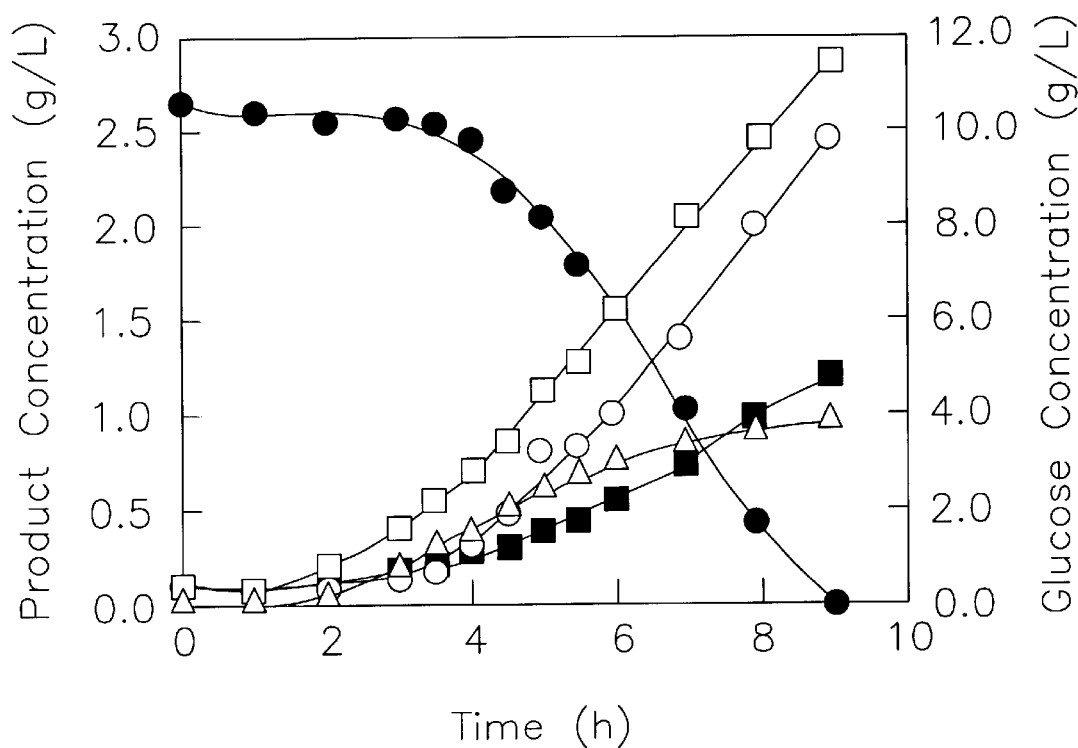
FIG. 10. Growth pattern and selected fermentation products of wild-type strain (MG1655) under strict anaerobic conditions in a glucose-limited (10 g/L) medium; concentrations of glucose (●), succinate (□), lactate (○), formate (□) and dry cell mass (Δ) were measured.
Figure 11:
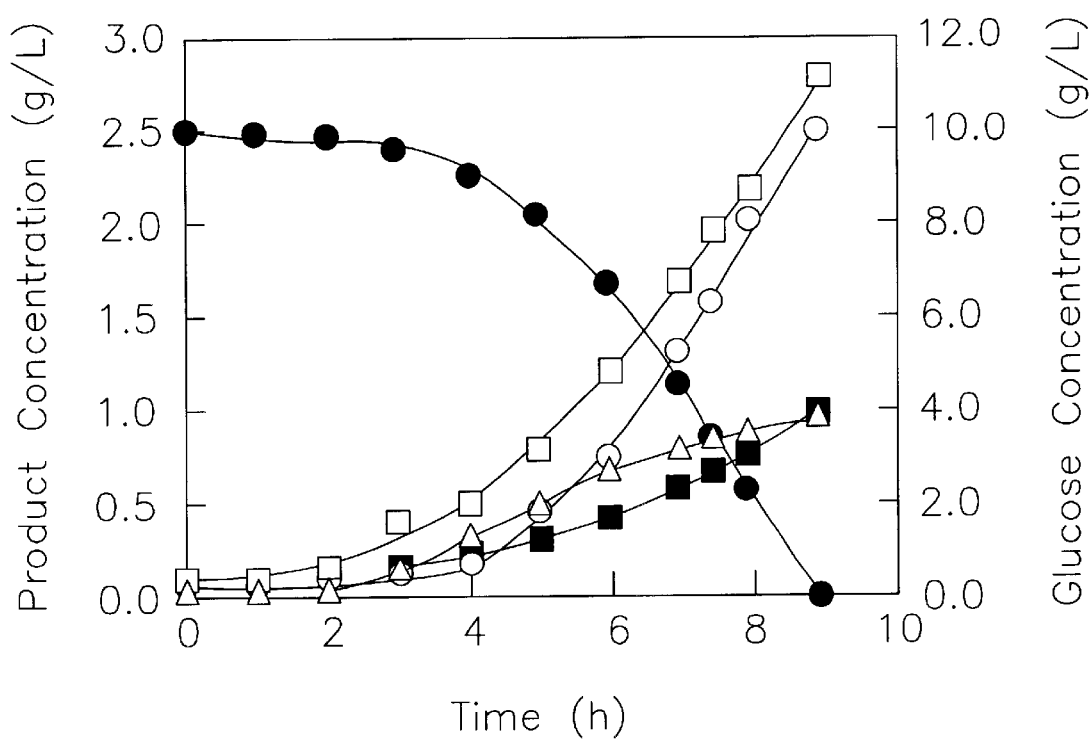
FIG. 11. Growth pattern and selected fermentation products of wild-type strain with pUC18 cloning/expression vector (MG1655/pUC18) under strict anaerobic conditions in a glucose-limited (10 g/L) medium; concentrations of glucose (●), succinate (■), lactate (○), formate (□) and dry cell mass (Δ) were measured.

*E. coli* MG1655 grew anaerobically with 10 g/L glucose as energy and carbon source to produce the end products shown in FIG. 2. The participation of phosphoenolpyruvate in glucose uptake is shown by the dashed line. The biochemical pathway is not stoichiometric nor are all cofactors shown. FIG. 10 shows the dry cell mass, succinate, lactate, formate and glucose concentrations with time in a typical 2-liter fermentation of this wild-type strain. FIG. 11 shows these concentrations with time in a fermentation of this wild-type strain with the cloning/expression vector pUC18. After complete glucose utilization, the average final concentration of succinate for the wild-type strain was 1.18 g/L, while for the wild-type strain with the vector pUC18 the final succinate concentration was 1.00 g/L. For these fermentations, the average final lactate concentration was 2.33 g/L for the wild-type strain and 2.27 g/L for the same strain with pUC18.

Figure 12:
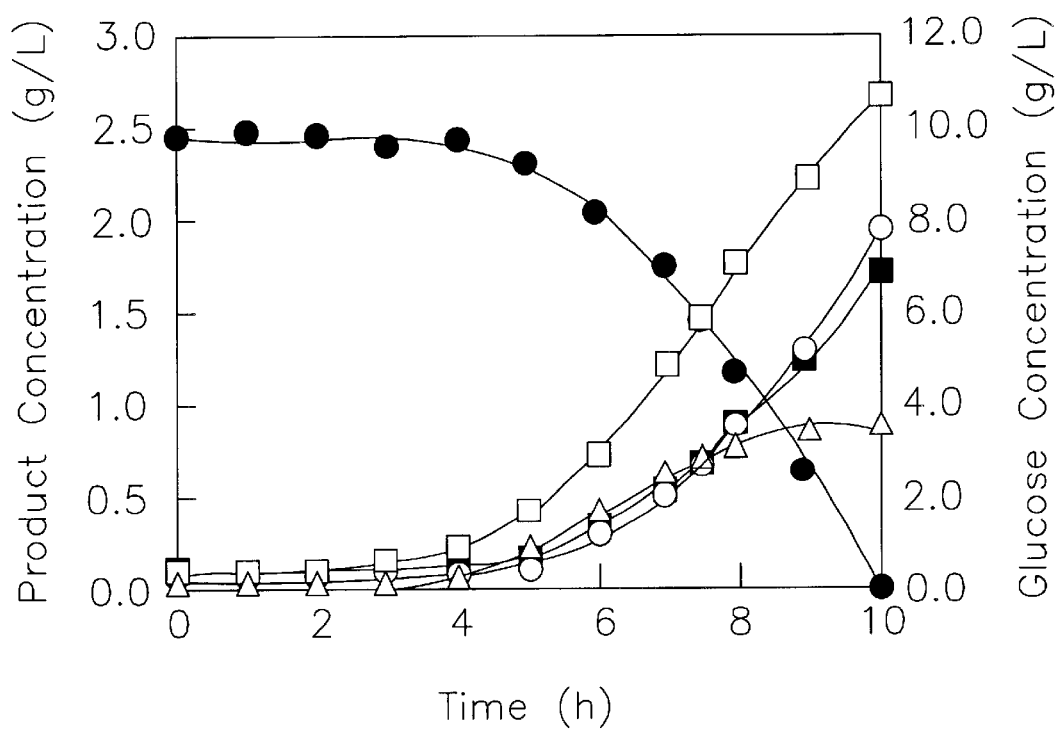
FIG. 12. Growth pattern and selected fermentation products of wild-type strain with pyc gene (MG1655/pUC18-pyc) under strict anaerobic conditions in a glucose-limited (10 g/L) medium; concentrations of glucose (●), succinate (■), lactate (○), formate (□) and dry cell mass (Δ) were measured.

FIG. 12 shows the concentrations with time of dry cell mass, succinate, lactate, formate and glucose in a fermentation of the strain containing the pUC18-pyc plasmid. This figure shows that the expression of pyruvate carboxylase causes a substantial increase in final succinate concentration and a decrease in lactate concentration. Specifically, for the wild-type with pUC18-pyc the average final succinate concentration was 1.77 g/L, while the average final lactate concentration was 1.88 g/L. These concentrations correspond to a 50% increase in succinate and about a 20% decrease in lactate concentration, indicating that carbon was diverted from lactate toward succinate formation in the presence of the pyruvate carboxylase.

The activities of PEP carboxylase and pyruvate carboxylase were assayed in cell-free extracts of the wild type and the plasmid-containing strains, and these results are shown in Table 5. In the wild type strain and the strain carrying the vector no pyruvate carboxylase activity was detected, while this activity was detected in MG1655/pUC18-pyc clone. PEP carboxylase activity was observed in all three strains.

TABLE 5

Enzyme activity in mid-logarithmic growth culture.

| | Sp. activity (μmol/min mg protein) | |
|---|---|---|
| Strain | Pyruvate carboxylase | PEP carboxylase |
| MG1655 | 0.0 | 0.10 |
| MG1655/pUC18 | 0.0 | 0.12 |
| MG1655/pUC18-pyc | 0.06 | 0.08 |

To determine the rates of glucose consumption, succinate production, and cell mass production during the fermentations, each set of concentration data was regressed to a fifth-order polynomial. (These best-fitting curves are shown in FIGS. 10–12 with the measured concentrations.) By taking the first derivative of this function with respect to time, an equation results which provides these rates as functions of time. This procedure is analogous to previous methods (E. Papoutsakis et al., *Biotechnol. Bioeng*, 27, 50–66 (1985); K. Reardon et al., *Biotechnol. Prog*, 3, 153–167 (1987)) used to calculate metabolic fluxes. In the case of fermentations with both pyruvate carboxylase and PEP carboxylase present, however, the flux analysis cannot be completed due to a mathematical singularity at the PEP/pyruvate nodes (S. Park et al., *Biotechnol. Bioeng*, 55, 864–879 (1997)). Nevertheless, using this approach the glucose uptake and the rates of succinate and cell mass production may be determined.

Table 6 shows the results of calculating the rates of glucose uptake, and succinate and cell mass production in a wild-type *E. coli* strain

TABLE 6

Rates of glucose uptake, succinate production, and cell production.

| Parameter | MG1655 | MG1655/pUC18 | MG1655/pUC18-pyc |
|---|---|---|---|
| Glucose uptake (maximum) | 2.17 (0.10) | 2.40 (0.01) | 2.47 (0.01) |
| Glucose uptake (average during final 4 h of fermentations) | 1.99 (0.05) | 2.00 (0.06) | 1.99 (0.05) |
| Rate of succinate production (at time of max. glucose uptake) | 0.234 (0.010) | 0.200 (0.012) | 0.426 (0.015) |

TABLE 6-continued

Rates of glucose uptake, succinate production, and cell production.

| Parameter | MG1655 | MG1655/pUC18 | MG1655/pUC18-pyc |
|---|---|---|---|
| Rate of succinate production (average during final 4 h) | 0.207 (0.005) | 0.177 (0.009) | 0.347 (0.002) |
| Cell production (maximum) | 0.213 (0.006) | 0.169 (0.033) | 0.199 (0.000) |

(MG1655), the wild-type strain with the pUC18 cloning/expression vector (MG1655/pUC18) and the wild-type strain with MG1655/pUC18-pyc. All units are g/Lh, and the values in parentheses represent standard deviation of measurements.

As these results demonstrate, the addition of the cloning vector or the vector with the pyc gene had no significant effect on the average glucose uptake during the final 4 hours of the fermentations. Indeed, the presence of the pyc gene actually increased the maximum glucose uptake about 14% from 2.17 g/Lh to 2.47 g/Lh. The presence of the pUC18 cloning vector reduced slightly the rates of succinate production. As expected from the data shown in FIG. 12, the expression of the pyc gene resulted in an 82% increase in succinate production at the time of maximum glucose uptake, and a 68% increase in the rate of succinate production during the final 4 hours of the fermentations. The maximum rate of cell growth (which occurred at 4–5 hours for each of the fermentations) was 0.213 g/Lh in the wild type strain, but decreased in the presence of pUC18 (0.169 g/Lh) or pUC18-pyc (0.199 g/Lh). Similarly, the overall cell yield was 0.0946 g dry cells/g glucose consumed for the wild-type, but 0.0895 g/g for the wild-type with pUC18 and 0.0882 g/g for the wild-type strain with pUC18-pyc. This decrease in biomass may be due to the expenditure of one mole of energy unit (ATP) per mole of pyruvate converted to oxaloacetate by pyruvate carboxylase and the increased demands of protein synthesis in the plasmid-containing strains. A specific cell growth rate could not be calculated since the growth of this strain shows logarithmic growth only for the first few hours of growth.

In summary, expression of pyruvate carboxylase from *R. etli* in *E. coli* causes a significant increase in succinate production at the expense of lactate production without affecting glucose uptake. This result has dramatic ramifications for bacterial fermentation processes which are used to produce oxaloacetate-derived biochemicals. Because overexpression of pyruvate carboxylase causes increased production of oxaloacetate-derived biochemicals without affecting glucose uptake, this technology can be advantageously employed in fermentation processes in order to obtain more product per amount of inputted glucose.

EXAMPLE IV

Expression of *R. etli* Pyruvate Carboxylase Causes Increased Threonine Production in *E. coli*

Materials and Methods

Bacterial strains and plasmids. The threonine-producing strain βIM-4 (ATCC 21277) was used in this study (Shiio and Nakamori, *Agr. Biol. Chem.*, 33, 1152–1160 (1969); I. Shiio et al. U.S. Pat. No. 3,580,810 (1971)). This strain was transformed with either pTrc99A-pyc (see Example II) or pTrc99A (E. Amann et al., *Gene*, 69, 301–315 (1988)).

Media and growth conditions. Aerobic fermentations were carried out in 2.0 L volume in Bioflow II Fermenters. The media used for these fermentation contained (per liter): glucose, 30.0 g; $(NH_4)_2SO_4$ 10.0 g, $FeSO_4 \cdot H_2O$, 10.0 mg; $MnSO_4 \cdot H_2O$, 5.5 mg/L; L-proline, 300 mg; L-isoleucine, 100 mg; L-methionine, 100 mg; $MgSO_4 \cdot 7H_2O$, 1 g; $KH_2PO_4$, 1 g; $CaCO_3$, 20 g; thiamine HCl, 1 mg; d-biotin, 1 mg. In order to maintain selective pressure for the plasmid-carrying strains, media were supplemented initially with 50 mg/L ampicillin. Also, IPTG was added to a final concentration of 1 mmol/L at 2 hours to fermentations performed with either of these strains.

Fermentation product analysis. Cell growth was determined by measuring optical density at 550 nm of a 1:21 dilution of sample in 0.1 M HCl. Glucose, acetic acid and other organic acids were analyzed by high-pressure liquid chromatography as previously described (Eiteman and Chastain, *Anal. Chim. Acta*, 338, 69–75 (1997)) using a Coregel 64-H ion-exclusion column. Threonine was quantified by high-pressure liquid chromatography using the ortho-phthaldialdehyde derivatization method (D. Hill, et al., *Anal. Chem.*, 51, 1338–1341 (1979); V. Svedas, et al. *Anal. Biochem.*, 101, 188–195 (1980)).

Results

Figure 13:
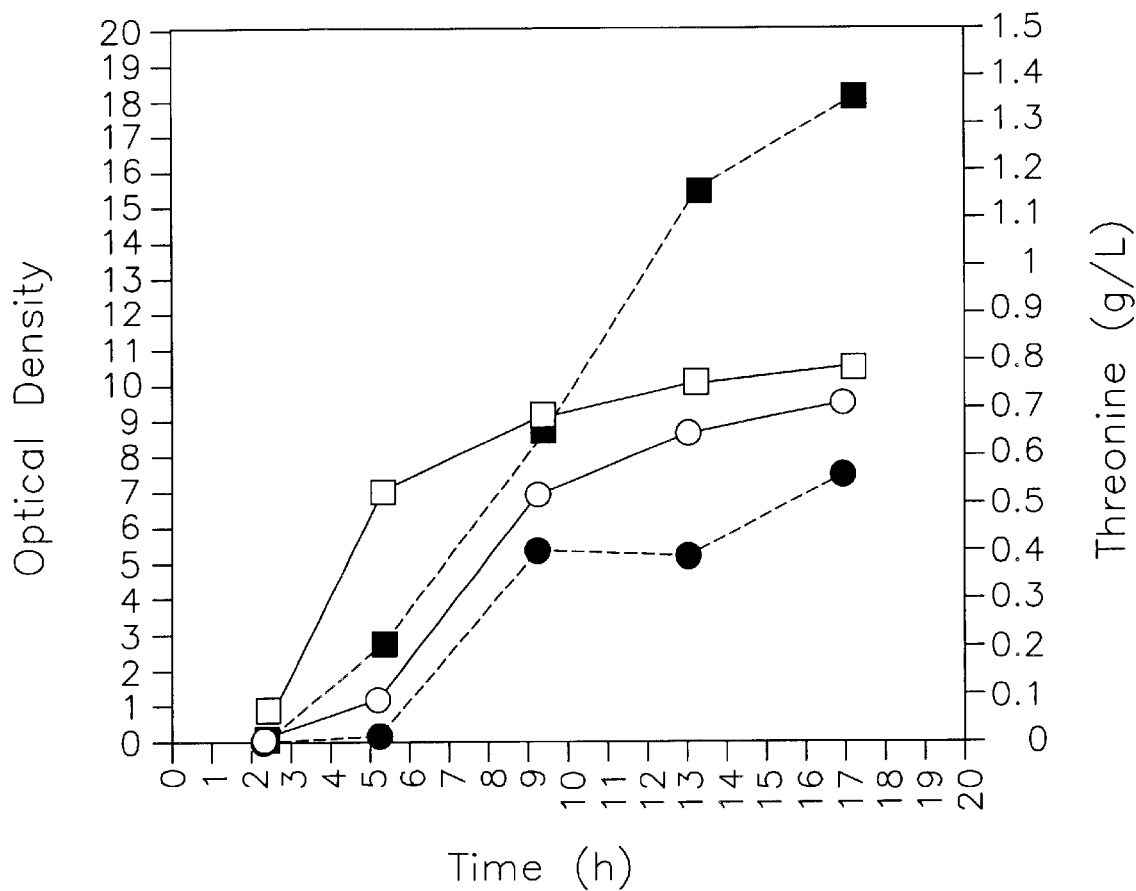
FIG. 13. Growth pattern and threonine production in the threonine producing strain βIM-4 (ATCC 21277) containing either pTrc99A or pTrc99A-pyc under strict aerobic conditions in a glucose-limited (30 g/L) medium; optical density in the pTrc99A containing strain (○), optical density in the pTrc99A-pyc containing strain (□), threonine concentrations in the pTrc99A containing strain (●), and threonine concentrations in the pTrc99A-pyc containing strain (■) were measured.

The threonine-producing strain βIM-4 (ATCC 21277), harboring either the control plasmid pTrc99A or the plasmid pTrc99A-pyc which overproduces pyruvate carboxylase, was grown aerobically with 30 g/L glucose as energy and carbon source and the production of threonine was measured. As shown in FIG. 13, the overproduction of pyruvate carboxylase caused a significant increase in the production of threonine in the threonine-producing *E. coli* strain. At 17 hours when the initial inputted glucose had been consumed, a concentration of 0.57 g/L threonine was detected in the parental strain harboring the pTrc99A control plasmid, while a concentration of 1.37 g/L threonine was detected in the parental strain harboring the pTrc99A-pyc plasmid. Given that the final $OD_{550}$ of both cultures were within 10% of each other at the end of the fermentation, the 240% increase in threonine concentration caused by the overproduction of pyruvate carboxylase can be deemed to be significant. As in our anaerobic fermentation studies (see Example III), we found that glucose uptake was not adversely affected by the overproduction of pyruvate carboxylase.

EXAMPLE V

Expression of *R. etli* Pyruvate Carboxylase from an *E. coli/C. Glutamicum* Shuttle Vector The *E. coli/C. glutamicum* shuttle vector pEKEX1 allows genes to be overexpressed in both *E. coli* and in *C. glutamicum*. Unfortunately, however, it only contains four restriction sites, EcoRI, BamHI, SalI and PstI, that can be used for cloning, three of which are already present in the *R. etli* pyc gene. For this reason, a derivative vector, pEKEX1A, was constructed which introduced a KpnI cloning site between the EcoRI and BamHI sites and a BglII cloning site between the BamHI and SalI sites. The following two oligonucleotides, 5' AAT TCG GTA CCG GAT CCA GAT CTG 3' (SEQ ID NO:1) and 5' TCG ACA GAT CTG GAT CCG GTA CCG 3' (SEQ ID NO:2), which were phosphorylated at their 5' ends, were annealed and ligated into the pEKEX1 vector which had been digested with BamHI and HindIII to create pEKEX1A. Restriction analysis was then performed to ensure that all the cloning sites were present in the new vector as expected. To construct pEKEX1A-pyc, a 3.5 kb KpnI, SalI fragment from pUC18-pyc that contained the pyc gene was ligated into the pEKEX1A vector which had been digested with the same to restriction enzymes. Successful expression from pEKEX1A was demonstrated in E. coli ALS225. Pyruvate carboxylase was detected via Western Blot analysis and the Payne and Morris pyruvate carboxylase activity assay. Because of the successful expression from the shuttle vector in E. coli, it is expected that an exogenouspyc gene can likewise be introduced into C. glutamicum to increase expression levels of pyruvate carboxylase in C. glutamicum as well.

EXAMPLE VI

Enhanced Synthesis of Lysine by C. glutamicum

C. glutamicum has long been the preferred microorganism for enzymatic production of lysine in the biochemicals industry. Naturally occurring strains of C. glutamicum make more of the oxaloacetate derived amino acids than many other known microbes. See Kirk et al., eds., Encyclopedia of Chemical Technology, 4th Ed., Vol. 2, pp. 534–570 (1992). Strains that are used commercially to make lysine are typically those wherein all biosynthetic branches after oxaloacetate which make any amino acid other than lysine have been knocked out, thus maximizing the biosynthesis of lysine. The enzyme pyruvate carboxylase has only recently been found in C. glutamicum, and it does not appear to be highly expressed when C. glutamicum is grown on media which uses glucose as the carbon source (P. Peters-Wendisch et al., Microbiology (Reading), 143, 1095–1103 (1997); M. Koffas et al., GenBank submission number AF038548 (submitted Dec. 14, 1997). Although it contains its own endogenous pyruvate carboxylase, a more convenient way to overexpress this enzyme in C. glutamicum is to insert the foreign gene pyc from R. etli. Accordingly, the current construct from pUC18 as described in Examples I and II will be transferred into C. glutamicum using the shuttle vector pEXO (G. Eikmanns et al., Gene, 102, 93–98 (1991)). Overexpression of pyruvate carboxylase in Corynebacterium glutamicum can also be achieved using the gene encoding pyruvate carboxylase from P. fluorescens. Carbon is expected to be diverted to lysine in an aerobic fermentation and increase lysine yield.

EXAMPLE VII

Enhanced Synthesis of Lysine by C glutamicum Auxotrophs

Recent evidence demonstrates that acetate, valine and alanine each accumulate in the latter stages of lysine synthesis in C. glutamicum (J. Vallino et al., Biotechnol. Bioeng., 41, 633–646 (1993)). Since each of these products is derived directly from pyruvate, this observation suggests that a bottleneck exists in the pathway at pyruvate (see FIG. 1). C. glutamicum that has been engineered according to the invention to overexpress pyruvate carboxylase already has an additional means of consuming pyruvate, and even more carbon can be diverted to lysine if one or more of these pathways are blocked. Alanine and valine auxotrophs and acetate-mutants of C. glutamicum can be engineered to overexpress pyruvate carboxylase according to the invention, to further enhance lysine yield.

EXAMPLE VIII

Enhanced Synthesis of Threonine in C. glutamicum

C. glutamicum can also be used to produce threonine, however, the strains that are used for the synthesis of threonine are different from the strains that are used for the synthesis of lysine. In the threonine-producing strains, all biosynthetic branches after oxaloacetate which make any amino acid other than threonine have been knocked out, thus maximizing the biosynthesis of threonine. Since the difference between lysine-producing and threonine-producing strains occurs after the oxaloacetate node, the metabolic engineering technology of the invention can equally be applied to the threonine-producing strains of C. glutamicum to enhance threonine synthesis. Synthesis of threonine is further enhanced in a C. glutamicum auxotroph as described above with in Example VI relating to lysine synthesis in C. glutamicum.

EXAMPLE IX

Enhancement of Biochemical Production Using Pyruvate Carboxylase from P. fluorescens One of the main reasons the metabolic network responsible for regulating the intracellular levels of oxaloacetate is so tightly controlled is due to the fact that the key enzymes which are involved in this process are both positively and negatively regulated. In most organisms such as R. etli, pyruvate carboxylase requires the positive effector molecule acetyl coenzyme A for its activation and is repressed due to feedback inhibition by aspartate (P. Attwood, Intl. J. Biochem. Cell Biol., 27, 231–249 (1995); M. Dunn et al., J. Bacteriol., 178, 5960–5970 (1996)). The benefits obtained from overproducing R. etli pyruvate carboxylase are thus limited by the fact that diverting carbon from pyruvate to oxaloacetate both depletes acetyl coenzyme A levels and increases aspartate levels. The pyruvate carboxylase from P. fluorescens, however, does not require acetyl coenzyme A for its activation and it is not affected by the feedback inhibition caused by aspartate (S. Milrad de Forchetti et al., J. Gen. Microbiol., 23, 75–81 (1976)). Overproduced P. fluorescens pyruvate carboxylase should allow even more carbon flow to be diverted towards oxaloacetate.

Because the genes encoding pyruvate carboxylases in bacteria appear to be highly homologous, the P. fluorescens pyc gene may be readily isolated from a genomic library using probes which have been prepared from the R. etli gene. The gene for pyruvate carboxylase in P. fluorescens will thus be identified, isolated, and cloned into an expression vector using standard genetic engineering techniques. Alternatively, the pyruvate carboxylase enzyme can be isolated and purified from P. fluorescens by following pyruvate carboxylase activity (as described in the above Examples) and also by assaying for biotinylated protein using Western blots. The N-terminal amino acid sequence of the purified protein is determined, then a degenerate oligonucleotide probe is made which is used to isolate the gene encoding pyruvate carboxylase from a genomic library that has been prepared from P. fluorescens. The pyc clone thus obtained is sequenced. From the sequence data, oligonucleotide primers are designed that allow cloning of this gene into an expression vector so that pyruvate carboxylase can be overproduced in the host cell. Either method can be used to yield a vector encoding the P. fluorescens pyc gene, which is then used to transform the host E. coli or C. glutamicum cell. Pyruvate carboxylase from P. fluorescens is expressed in the host cell, and biochemical production is enhanced as described in the preceding examples.

EXAMPLE X

Enhancement of Biochemical Production By Overexpression of Both Pyruvate Carboxylase and PEP Carboxylase In many organisms PEP can be carboxylated to oxaloacetate via PEP carboxylase or it can be converted to pyruvate by pyruvate kinase (I. Shiio et al., J. Biochem., 48, 110–120 (1960); M. Jetten et al., Appl. Microbiol. Biotechnol., 41, 47–52 (1994)). One possible strategy that was tried to increase the carbon flux toward oxaloacetate in C. glutamicum was to block the carbon flux from PEP toward pyruvate (see FIG. 3). However, lysine production by pyruvate kinase mutants was 40% lower than by a parent strain, indicating that pyruvate is essential for high-level lysine production (M. Gubler et al., Appl. Microbiol. Biotechnol., 40, 57–63 (1994)).

Carbon flux toward oxaloacetate may be increased by overexpressing PEP carboxylase in conjunction with overexpressed pyruvate carboxylase without concomitantly blocking carbon flux from PEP to pyruvate or affecting glucose uptake.

heterologous enzyme can be used to increase the carbon flux towards oxaloacetate in C. glutamicum. The genes encoding PEP carboxylase in A. nidulans have been isolated and cloned (T. Kodaki et al., J. Biochem., 97, 533–539 (1985)).

EXAMPLE XI

Enhancement of Biochemical Production By Disrupting the pck Gene Encoding PEP Carboxykinase in Conjunction with Overexpressed Pyruvate Carboxylase Some of carbon which is diverted to oxaloacetate via overproduced pyruvate carboxylase is likely converted back to PEP due to the presence of PEP carboxykinase. More carbon can be diverted towards oxaloacetate in these systems if the host cell contains a disrupted pck gene, such as an E. coli strain which contains a pck null allele (e.g., A. Goldie, J. Bacteriol., 141, 1115–1121 (1980)).

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

```
                         SEQUENCE LISTING

<160> NUMBER OF SEQ ID NOS:  2

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence:  forward
      primer

<400> SEQUENCE: 1
tactatggta ccttaggaaa cagctatgcc catatccaag atactcgtt              49

<210> SEQ ID NO 2
<211> LENGTH: 49
<212> TYPE: DNA
<213> ORGANISM: Artificial Sequence
<220> FEATURE:
<223> OTHER INFORMATION: Description of Artificial Sequence:  reverse
      primer

<400> SEQUENCE: 2
attcgtactc aggatctgaa agatctaaca gcctgacttt acacaatcg              49
```

In heterotrophs such as C. glutamicum, however, PEP carboxylase requires acetyl-CoA for its activation, and is inhibited by aspartate (M. Jetten et al., Annals NY Acad. Sci. 272, 12–29 (1993)); hence amplification of C. glutamicum PEP carboxylase genes has not resulted in increased lysine yield (J. Cremer et al., Appl. Environ. Microbiol., 57, 1746–1752 (1991)). PEP carboxylase isolated from the cyanobacteria Anacystis nidulans, however, does not require acetyl CoA for activation nor is it inhibited by aspartate (M. Utter et al., Enzymes, 6, 117–135 (1972)). Therefore, this

What is claimed is:

1. A metabolically engineered E. coli cell transformed with a polynucleotide sequence encoding a pyruvate carboxylase operatively linked to a promoter, wherein said polynucleotide sequence is expressed and produces an enzymatically active pyruvate carboxylase.

2. The metabolically engineered E. coil cell of claim 1 wherein the pyruvate carboxylase is a Rhizobium etli pyruvate carboxylase.

3. A metabolically engineered *E. coli* cell transformed with a polynucleotide sequence encoding a pyruvate carboxylase operatively linked to a promoter; wherein the cell comprises enzymatically active pyruvate carboxylase and wherein the polynucleotide sequence is chromosomally integrated.

4. A method for making a metabolically engineered *E. coli* cell comprising transforming an *E. coli* cell with a polynucleotide sequence encoding a pyruvate carboxylase operatively linked to a promoter to yield a metabolically engineered *E. coli* cell that comprises enzymatically active pyruvate carboxylase.

5. A method for making succinate comprising:
   (a) providing a first *E. coli* cell that produces succinate;
   (b) transforming the first *E. coli* cell with a polynucleotide sequence encoding a pyruvate carboxylase operatively linked to a promoter to yield a metabolically engineered *E. coli* cell;
   (c) culturing the metabolically engineered *E. coli* cell to permit expression of the pyruvate carboxylase to cause increased production of succinate relative to a second *E. coli* cell that has not been transformed with the polynucleotide sequence encoding a pyruvate carboxylase operatively linked to a promoter; and
   (d) isolating the succinate produced by the metabolically engineered *E. coli* cell.

6. The method of claim 5 wherein step (b) comprises transforming the cell with a nucleic acid fragment comprising an *R. etli* gene encoding pyruvate carboxylase.

7. A method for making succinate comprising:
   (a) providing a first, metabolically engineered *E. coli* cell that produces succinate, wherein the metabolically engineered *E. coli* cell has been transformed with a polynucleotide sequence encoding a pyruvate carboxylase operatively linked to a promoter;
   (b) culturing the metabolically engineered *E. coli* cell under conditions that permit expression of the pyruvate carboxylase to cause increased production of succinate relative to a second *E. coli* cell that has not been transformed with the polynucleotide sequence encoding a pyruvate carboxylase operatively linked to a promoter; and
   (c) isolating the succinate produced by the metabolically engineered *E. coli* cell.

8. A method for making threonine comprising:
   (a) providing a firsts metabolically engineered *E. coli* cell that produces threonine, wherein the metabolically engineered *E. coli* cell has been transformed with a polynucleotide sequence encoding a pyruvate carboxylase operatively linked to a promoter,
   (b) culturing the metabolically engineered *E. coli* cell under conditions that permit expression of pyruvate carboxylase to cause increased production of threonine relative to a second *E. coli* cell that has not been transformed with a polynucleotide sequence encoding a pyruvate carboxylase operatively linked to a promoter; and
   (c) isolating the threonine produced by the metabolically engineered *E. coli* cell.

9. A method for making threonine comprising:
   (a) providing first *E. coli* cell that produces threonine;
   (b) transforming the first *E. coli* cell with a polynucleotide sequence encoding a pyruvate carboxylase operatively linked to a promoter to yield a metabolically engineered *E. coli* cell;
   (c) culturing the metabolically engineered *E. coli* cell to permit expression of the pyruvate carboxylase to cause increased production of threonine relative to a second *E. coli* cell that has not been transformed with the polynucleotide sequence encoding a pyruvate carboxylase operatively linked to a promoter; and
   (d) isolating the threonine produced by the metabolically engineered *E. coli* cell.

10. The method of claim 9 wherein step (b) comprises transforming the cell with a nucleic acid fragment comprising an *R. etli* gene encoding pyruvate carboxylase.

* * * * *